United States Patent [19]
Sakano

[11] Patent Number: 5,834,208
[45] Date of Patent: Nov. 10, 1998

[54] TYROSINE KINASE

[75] Inventor: Seiji Sakano, Fuji, Japan

[73] Assignee: Asahi Kasei Kogyo Kabushiki Kaisha, Osaka, Japan

[21] Appl. No.: 604,989

[22] PCT Filed: Aug. 25, 1994

[86] PCT No.: PCT/JP94/01411

§ 371 Date: Feb. 23, 1996

§ 102(e) Date: Feb. 23, 1996

[87] PCT Pub. No.: WO95/06113

PCT Pub. Date: Mar. 2, 1995

[30] Foreign Application Priority Data

Aug. 25, 1993 [JP] Japan .................................. 5-210403
Mar. 29, 1994 [JP] Japan .................................. 6-058553

[51] Int. Cl.$^6$ ............................. C12Q 1/48; C12N 15/54; C12N 15/63
[52] U.S. Cl. ..................... 435/7.1; 435/194; 435/320.1; 536/235; 530/350
[58] Field of Search ...................... 435/7.1, 194, 320.1; 536/23.5; 550/350

[56] References Cited

U.S. PATENT DOCUMENTS 5,618,829  4/1997  Takayangi et al. .................... 514/332

FOREIGN PATENT DOCUMENTS

WO 93/15201  8/1993  WIPO .

OTHER PUBLICATIONS

Bennett, et al. J. Biol. Chem. vol. 269. No. 2. pp. 1068–1074 1994.
Accession No.:T06085 ESTTD03974 Homo Sapiens cDNA clone HFBD023 Situation to e–Sre Kinase. Adams et al. Nature Genetics vol. 4 pp. 256–267 (1993).
MeVicar et al. Oncogene vol. 9, pp. 2037–2044 (1994).
Sakano et al. Oncogene vol. 9. pp. 1155–1161 (1994).
"The Protein Kinase Family: Conserved Features and Deduced Phylogeny of the Catalytic Domains" Steven K. Hanks, et al., reported in Science, vol. 241, Jul. 1, 1988, pp. 42–51 (English reference).
"Two putative protein–tyrosine kinases identified by application of the polymerase chain reaction" by Andrew F. Wilks, reported in Proc. Natl. Acad. Sci., vol. 86, Mar. 1989, pp. 1603–1607 (English reference).
"Cloning of a complementary DNA for a protein for a protein–tyrosine kinase that specifically phosphorylates a negative regulatory site of p60$^{c-src}$", reported in Nature, vol. 351, May 2, 1991, pp. 69–72 (English reference). Nada et al.

Primary Examiner—Stephen Walsh
Assistant Examiner—Daryl A. Basham
Attorney, Agent, or Firm—Pennie & Edmonds LLP

[57] ABSTRACT

Disclosed are a novel cytoplasmic tyrosine kinase which is increased with respect to expression amount thereof in accordance with the differentiation of blood cells, and a deoxyribonucleic acid (DNA) coding for the same. The tyrosine kinase of the present invention can be advantageously used for screening chemical substances having the capability to inhibit or activate the tyrosine kinase activity of at least the tyrosine kinase of the present invention. Also disclosed are a replicable recombinant DNA molecule comprising a replicable expression vector and, operably inserted in the vector, a DNA coding for the tyrosine kinase of the present invention; a microorganism or animal cells transformed with the replicable recombinant DNA molecule; an antibody reactive with a polypeptide comprising as an immunogen at least part of an amino acid sequence of the tyrosine kinase of the present invention; a sense DNA prepared from the cDNA coding for the tyrosine kinase of the present invention and an anti-sense DNA which is complementary to the sense DNA; and a sense RNA prepared from the cDNA coding for the tyrosine kinase of the present invention and an anti-sense RNA which is complementary to the sense RNA.

5 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 64 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: human
        ( B ) STRAIN: UT-7

( x i ) SEQUENCE DESCRIPTION: SEQ ID NO:1:

```
Ala  Pro  Gly  Thr  Gln  Cys  Ile  Thr  Lys  Cys  Glu  His  Thr  Arg  Pro  Lys
 1                   5                        10                       15
Pro  Gly  Glu  Leu  Ala  Phe  Arg  Lys  Gly  Asp  Val  Val  Thr  Ile  Leu  Glu
               20                       25                       30
Ala  Cys  Glu  Asn  Lys  Ser  Trp  Tyr  Arg  Val  Lys  His  His  Thr  Ser  Gly
          35                       40                       45
Gln  Glu  Gly  Leu  Leu  Ala  Ala  Gly  Ala  Leu  Arg  Glu  Arg  Glu  Ala  Leu
          50                       55                  60
```

( 2 ) INFORMATION FOR SEQ ID NO:2:

( i ) SEQUENCE CHARACTERISTICS:
        ( A ) LENGTH: 75 amino acids
        ( B ) TYPE: amino acid
        ( C ) TOPOLOGY: linear ( i i ) MOLECULE TYPE: protein ( v i ) ORIGINAL SOURCE:
        ( A ) ORGANISM: human
        ( B ) STRAIN: UT-7

( x i ) SEQUENCE DESCRIPTION: SEQ ID NO:2:

```
Trp  Phe  His  Gly  Lys  Ile  Ser  Gly  Gln  Glu  Ala  Val  Gln  Gln  Leu  Gln
 1                   5                        10                       15
Pro  Pro  Glu  Asp  Gly  Leu  Phe  Leu  Val  Arg  Glu  Ser  Ala  Arg  His  Pro
               20                       25                       30
```

```
Gly Asp Tyr Val Leu Cys Val Ser Phe Gly Arg Asp Val Ile His Tyr
         35                  40                  45

Arg Val Leu His Arg Asp Gly His Leu Thr Ile Asp Glu Ala Val Phe
     50                  55                  60

Phe Cys Asn Leu Met Asp Met Val Glu His Tyr
 65                  70                  75
```

(2) INFORMATION FOR SEQ ID NO:3:

(i) SEQUENCE CHARACTERISTICS:
        (A) LENGTH: 246 amino acids
        (B) TYPE: amino acid
        (C) TOPOLOGY: linear (ii) MOLECULE TYPE: protein (vi) ORIGINAL SOURCE:
        (A) ORGANISM: human
        (B) STRAIN: UT-7

(xi) SEQUENCE DESCRIPTION: SEQ ID NO:3:

```
Gln His Leu Thr Leu Gly Ala Gln Ile Gly Glu Gly Glu Phe Gly Ala
 1               5                  10                  15

Val Leu Gln Gly Glu Tyr Leu Gly Gln Lys Val Ala Val Lys Asn Ile
         20                  25                  30

Lys Cys Asp Val Thr Ala Gln Ala Phe Leu Asp Glu Thr Ala Val Met
         35                  40                  45

Thr Lys Met Gln His Glu Asn Leu Val Arg Leu Leu Gly Val Ile Leu
     50                  55                  60

His Gln Gly Leu Tyr Ile Val Met Glu His Val Ser Lys Gly Asn Leu
 65                  70                  75                  80

Val Asn Phe Leu Arg Thr Arg Gly Arg Ala Leu Val Asn Thr Ala Gln
                 85                  90                  95

Leu Leu Gln Phe Ser Leu His Val Ala Glu Gly Met Glu Tyr Leu Glu
             100                 105                 110

Ser Lys Lys Leu Val His Arg Asp Leu Ala Ala Arg Asn Ile Leu Val
         115                 120                 125

Ser Glu Asp Leu Val Ala Lys Val Ser Asp Phe Gly Leu Ala Lys Ala
     130                 135                 140

Glu Arg Lys Gly Leu Asp Ser Ser Arg Leu Pro Val Lys Trp Thr Ala
145                 150                 155                 160

Pro Glu Ala Leu Lys His Gly Lys Phe Thr Ser Lys Ser Asp Val Trp
                 165                 170                 175

Ser Phe Gly Val Leu Leu Trp Glu Val Phe Ser Tyr Gly Arg Ala Pro
             180                 185                 190

Tyr Pro Lys Met Ser Leu Lys Glu Val Ser Glu Ala Val Glu Lys Gly
         195                 200                 205

Tyr Arg Met Glu Pro Pro Glu Gly Cys Pro Gly Pro Val His Val Leu
     210                 215                 220

Met Ser Ser Cys Trp Glu Ala Glu Pro Ala Arg Arg Pro Pro Phe Arg
225                 230                 235                 240

Lys Leu Ala Glu Lys Leu
                 245
```

(2) INFORMATION FOR SEQ ID NO:4:

(i) SEQUENCE CHARACTERISTICS:
        (A) LENGTH: 466 amino acids
        (B) TYPE: amino acid
        (C) TOPOLOGY: linear ( i i ) MOLECULE TYPE: protein ( v i ) ORIGINAL SOURCE:
    ( A ) ORGANISM: human
    ( B ) STRAIN: UT-7

( x i ) SEQUENCE DESCRIPTION: SEQ ID NO:4:

| Met | Pro | Thr | Arg | Arg | Trp | Ala | Pro | Gly | Thr | Gln | Cys | Ile | Thr | Lys | Cys |
|---|---|---|---|---|---|---|---|---|---|---|---|---|---|---|---|
| 1 | | | | 5 | | | | | 10 | | | | | 15 | |
| Glu | His | Thr | Arg | Pro | Lys | Pro | Gly | Glu | Leu | Ala | Phe | Arg | Lys | Gly | Asp |
| | | | 20 | | | | | 25 | | | | | 30 | | |
| Val | Val | Thr | Ile | Leu | Glu | Ala | Cys | Glu | Asn | Lys | Ser | Trp | Tyr | Arg | Val |
| | | 35 | | | | | 40 | | | | | 45 | | | |
| Lys | His | His | Thr | Ser | Gly | Gln | Glu | Gly | Leu | Leu | Ala | Ala | Gly | Ala | Leu |
| | 50 | | | | | 55 | | | | | | 60 | | | |
| Arg | Glu | Arg | Glu | Ala | Leu | Ser | Ala | Asp | Pro | Lys | Leu | Ser | Leu | Met | Pro |
| 65 | | | | | 70 | | | | | 75 | | | | | 80 |
| Trp | Phe | His | Gly | Lys | Ile | Ser | Gly | Gln | Glu | Ala | Val | Gln | Gln | Leu | Gln |
| | | | | 85 | | | | | 90 | | | | | 95 | |
| Pro | Pro | Glu | Asp | Gly | Leu | Phe | Leu | Val | Arg | Glu | Ser | Ala | Arg | His | Pro |
| | | | 100 | | | | | 105 | | | | | 110 | | |
| Gly | Asp | Tyr | Val | Leu | Cys | Val | Ser | Phe | Gly | Arg | Asp | Val | Ile | His | Tyr |
| | | | 115 | | | | 120 | | | | | 125 | | | |
| Arg | Val | Leu | His | Arg | Asp | Gly | His | Leu | Thr | Ile | Asp | Glu | Ala | Val | Phe |
| | 130 | | | | | 135 | | | | | | 140 | | | |
| Phe | Cys | Asn | Leu | Met | Asp | Met | Val | Glu | His | Tyr | Ser | Lys | Asp | Lys | Gly |
| 145 | | | | | 150 | | | | | 155 | | | | | 160 |
| Ala | Ile | Cys | Thr | Lys | Leu | Val | Arg | Pro | Lys | Arg | Lys | His | Gly | Thr | Lys |
| | | | | 165 | | | | | 170 | | | | | 175 | |
| Ser | Ala | Glu | Glu | Glu | Leu | Ala | Arg | Ala | Gly | Trp | Leu | Leu | Asn | Leu | Gln |
| | | | | 180 | | | | | 185 | | | | | 190 | |
| His | Leu | Thr | Leu | Gly | Ala | Gln | Ile | Gly | Glu | Gly | Glu | Phe | Gly | Ala | Val |
| | | | 195 | | | | | 200 | | | | | 205 | | |
| Leu | Gln | Gly | Glu | Tyr | Leu | Gly | Gln | Lys | Val | Ala | Val | Lys | Asn | Ile | Lys |
| | 210 | | | | | 215 | | | | | | 220 | | | |
| Cys | Asp | Val | Thr | Ala | Gln | Ala | Phe | Leu | Asp | Glu | Thr | Ala | Val | Met | Thr |
| 225 | | | | | 230 | | | | | 235 | | | | | 240 |
| Lys | Met | Gln | His | Glu | Asn | Leu | Val | Arg | Leu | Leu | Gly | Val | Ile | Leu | His |
| | | | | 245 | | | | | 250 | | | | | 255 | |
| Gln | Gly | Leu | Tyr | Ile | Val | Met | Glu | His | Val | Ser | Lys | Gly | Asn | Leu | Val |
| | | | | 260 | | | | | 265 | | | | | 270 | |
| Asn | Phe | Leu | Arg | Thr | Arg | Gly | Arg | Ala | Leu | Val | Asn | Thr | Ala | Gln | Leu |
| | | | 275 | | | | | 280 | | | | | 285 | | |
| Leu | Gln | Phe | Ser | Leu | His | Val | Ala | Glu | Gly | Met | Glu | Tyr | Leu | Glu | Ser |
| | 290 | | | | | 295 | | | | | 300 | | | | |
| Lys | Lys | Leu | Val | His | Arg | Asp | Leu | Ala | Ala | Arg | Asn | Ile | Leu | Val | Ser |
| 305 | | | | | 310 | | | | | 315 | | | | | 320 |
| Glu | Asp | Leu | Val | Ala | Lys | Val | Ser | Asp | Phe | Gly | Leu | Ala | Lys | Ala | Glu |
| | | | | 325 | | | | | 330 | | | | | 335 | |
| Arg | Lys | Gly | Leu | Asp | Ser | Ser | Arg | Leu | Pro | Val | Lys | Trp | Thr | Ala | Pro |
| | | | 340 | | | | | 345 | | | | | 350 | | |
| Glu | Ala | Leu | Lys | His | Gly | Lys | Phe | Thr | Ser | Lys | Ser | Asp | Val | Trp | Ser |
| | | | 355 | | | | | 360 | | | | | 365 | | |
| Phe | Gly | Val | Leu | Leu | Trp | Glu | Val | Phe | Ser | Tyr | Gly | Arg | Ala | Pro | Tyr |
| | 370 | | | | | 375 | | | | | | 380 | | | |

| Pro | Lys | Met | Ser | Leu | Lys | Glu | Val | Ser | Glu | Ala | Val | Glu | Lys | Gly | Tyr |
| 385 | | | | | 390 | | | | 395 | | | | | | 400 |

| Arg | Met | Glu | Pro | Pro | Glu | Gly | Cys | Pro | Gly | Pro | Val | His | Val | Leu | Met |
| | | | | 405 | | | | | 410 | | | | | 415 | |

| Ser | Ser | Cys | Trp | Glu | Ala | Glu | Pro | Ala | Arg | Arg | Pro | Pro | Phe | Arg | Lys |
| | | | 420 | | | | | 425 | | | | | 430 | | |

| Leu | Ala | Glu | Lys | Leu | Ala | Arg | Glu | Leu | Arg | Ser | Ala | Gly | Ala | Pro | Ala |
| | | 435 | | | | | 440 | | | | | 445 | | | |

| Ser | Val | Ser | Gly | Gln | Asp | Ala | Asp | Gly | Ser | Thr | Ser | Pro | Arg | Ser | Gln |
| | 450 | | | | | 455 | | | | | 460 | | | | |

| Glu | Pro |
| 465 | |

(2) INFORMATION FOR SEQ ID NO:5:

(i) SEQUENCE CHARACTERISTICS:
        (A) LENGTH: 507 amino acids
        (B) TYPE: amino acid
        (C) TOPOLOGY: linear (ii) MOLECULE TYPE: protein (vi) ORIGINAL SOURCE:
        (A) ORGANISM: human
        (B) STRAIN: UT-7

(xi) SEQUENCE DESCRIPTION: SEQ ID NO:5:

| Met | Ala | Gly | Arg | Gly | Ser | Leu | Val | Ser | Trp | Arg | Ala | Phe | His | Gly | Cys |
| 1 | | | | 5 | | | | | 10 | | | | | 15 | |

| Asp | Ser | Ala | Glu | Glu | Leu | Pro | Arg | Val | Ser | Pro | Arg | Phe | Leu | Arg | Ala |
| | | | 20 | | | | | 25 | | | | | 30 | | |

| Trp | His | Pro | Pro | Pro | Val | Ser | Ala | Arg | Met | Pro | Thr | Arg | Arg | Trp | Ala |
| | | 35 | | | | | 40 | | | | | 45 | | | |

| Pro | Gly | Thr | Gln | Cys | Ile | Thr | Lys | Cys | Glu | His | Thr | Arg | Pro | Lys | Pro |
| | 50 | | | | | 55 | | | | | 60 | | | | |

| Gly | Glu | Leu | Ala | Phe | Arg | Lys | Gly | Asp | Val | Val | Thr | Ile | Leu | Glu | Ala |
| 65 | | | | | 70 | | | | | 75 | | | | | 80 |

| Cys | Glu | Asn | Lys | Ser | Trp | Tyr | Arg | Val | Lys | His | His | Thr | Ser | Gly | Gln |
| | | | | 85 | | | | | 90 | | | | | 95 | |

| Glu | Gly | Leu | Leu | Ala | Ala | Gly | Ala | Leu | Arg | Glu | Arg | Glu | Ala | Leu | Ser |
| | | | 100 | | | | | 105 | | | | | 110 | | |

| Ala | Asp | Pro | Lys | Leu | Ser | Leu | Met | Pro | Trp | Phe | His | Gly | Lys | Ile | Ser |
| | | | 115 | | | | | 120 | | | | | 125 | | |

| Gly | Gln | Glu | Ala | Val | Gln | Gln | Leu | Gln | Pro | Pro | Glu | Asp | Gly | Leu | Phe |
| | | 130 | | | | | 135 | | | | | 140 | | | |

| Leu | Val | Arg | Glu | Ser | Ala | Arg | His | Pro | Gly | Asp | Tyr | Val | Leu | Cys | Val |
| 145 | | | | | 150 | | | | | 155 | | | | | 160 |

| Ser | Phe | Gly | Arg | His | Val | Ile | His | Tyr | Arg | Val | Leu | His | Arg | Asp | Gly |
| | | | | 165 | | | | | 170 | | | | | 175 | |

| His | Leu | Thr | Ile | Asp | Glu | Ala | Val | Phe | Phe | Cys | Asn | Leu | Met | Asp | Met |
| | | | 180 | | | | | 185 | | | | | 190 | | |

| Val | Glu | His | Tyr | Ser | Lys | Asp | Lys | Gly | Ala | Ile | Cys | Thr | Lys | Leu | Val |
| | | 195 | | | | | 200 | | | | | 205 | | | |

| Arg | Pro | Lys | Arg | Lys | His | Gly | Thr | Lys | Ser | Ala | Glu | Glu | Glu | Leu | Ala |
| | 210 | | | | | 215 | | | | | 220 | | | | |

| Arg | Ala | Gly | Trp | Leu | Leu | Asn | Leu | Gln | His | Leu | Thr | Leu | Gly | Ala | Gln |
| 225 | | | | | 230 | | | | | 235 | | | | | 240 |

-continued

| | | | | | | | | | | | | | | |
|---|---|---|---|---|---|---|---|---|---|---|---|---|---|---|
| Ile | Gly | Glu | Gly | Glu | Phe | Gly | Ala | Val | Leu | Gln | Gly | Glu | Tyr | Leu | Gly |
| | | | | 245 | | | | | 250 | | | | | 255 | |
| Gln | Lys | Val | Ala | Val | Lys | Asn | Ile | Lys | Cys | Asp | Val | Thr | Ala | Gln | Ala |
| | | | 260 | | | | | 265 | | | | | 270 | | |
| Phe | Leu | Asp | Glu | Thr | Ala | Val | Met | Thr | Lys | Met | Gln | His | Glu | Asn | Leu |
| | | 275 | | | | | 280 | | | | | 285 | | | |
| Val | Arg | Leu | Leu | Gly | Val | Ile | Leu | His | Gln | Gly | Leu | Tyr | Ile | Val | Met |
| | 290 | | | | | 295 | | | | | 300 | | | | |
| Glu | His | Val | Ser | Lys | Gly | Asn | Leu | Val | Asn | Phe | Leu | Arg | Thr | Arg | Gly |
| 305 | | | | | 310 | | | | 315 | | | | | | 320 |
| Arg | Ala | Leu | Val | Asn | Thr | Ala | Gln | Leu | Leu | Gln | Phe | Ser | Leu | His | Val |
| | | | | 325 | | | | | 330 | | | | | 335 | |
| Ala | Glu | Gly | Met | Glu | Tyr | Leu | Glu | Ser | Lys | Lys | Leu | Val | His | Arg | Asp |
| | | | 340 | | | | | 345 | | | | | 350 | | |
| Leu | Ala | Ala | Arg | Asn | Ile | Leu | Val | Ser | Glu | Asp | Leu | Val | Ala | Lys | Val |
| | | | 355 | | | | | 360 | | | | | 365 | | |
| Ser | Asp | Phe | Gly | Leu | Ala | Lys | Ala | Glu | Arg | Lys | Gly | Leu | Asp | Ser | Ser |
| | 370 | | | | | 375 | | | | | 380 | | | | |
| Arg | Leu | Pro | Val | Lys | Trp | Thr | Ala | Pro | Glu | Ala | Leu | Lys | His | Gly | Lys |
| 385 | | | | | 390 | | | | | 395 | | | | | 400 |
| Phe | Thr | Ser | Lys | Ser | Asp | Val | Trp | Ser | Phe | Gly | Val | Leu | Leu | Trp | Glu |
| | | | | 405 | | | | | 410 | | | | | 415 | |
| Val | Phe | Ser | Tyr | Gly | Arg | Ala | Pro | Tyr | Pro | Lys | Met | Ser | Leu | Lys | Glu |
| | | | 420 | | | | | 425 | | | | | 430 | | |
| Val | Ser | Glu | Ala | Val | Glu | Lys | Gly | Tyr | Arg | Met | Glu | Pro | Pro | Glu | Gly |
| | | | 435 | | | | | 440 | | | | | 445 | | |
| Cys | Pro | Gly | Pro | Val | His | Val | Leu | Met | Ser | Ser | Cys | Trp | Glu | Ala | Glu |
| | | | 450 | | | | | 455 | | | | | 460 | | |
| Pro | Ala | Arg | Arg | Pro | Pro | Phe | Arg | Lys | Leu | Ala | Glu | Lys | Leu | Ala | Arg |
| 465 | | | | | 470 | | | | | 475 | | | | | 480 |
| Glu | Leu | Arg | Ser | Ala | Gly | Ala | Pro | Ala | Ser | Val | Ser | Gly | Gln | Asp | Ala |
| | | | | 485 | | | | | 490 | | | | | 495 | |
| Asp | Gly | Ser | Thr | Ser | Pro | Arg | Ser | Gln | Glu | Pro | | | | | |
| | | | 500 | | | | | 505 | | | | | | | |

( 2 ) INFORMATION FOR SEQ ID NO:6:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: human
        ( B ) STRAIN: UT-7

( x i ) SEQUENCE DESCRIPTION: SEQ ID NO:6:

| | | | | | |
|---|---|---|---|---|---|
| GCCCCGGGCA | CCCAGTGTAT | CACCAAATGC | GAGCACACCC | GCCCCAAGCC | AGGGGAGCTG | 60 |
| GCCTTCCGCA | AGGGCGACGT | GGTCACCATC | CTGGAGGCCT | GCGAGAACAA | GAGCTGGTAC | 120 |
| CGCGTCAAGC | ACCACACCAG | TGGACAGGAG | GGGCTGCTGG | CAGCTGGGGC | GCTGCGGGAG | 180 |
| CGGGAGGCCC | TC | | | | | 192 |

( 2 ) INFORMATION FOR SEQ ID NO:7:

( i ) SEQUENCE CHARACTERISTICS:

-continued (A) LENGTH: 225 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: human
(B) STRAIN: UT-7

(xi) SEQUENCE DESCRIPTION: SEQ ID NO:7:

| | | | | | |
|---|---|---|---|---|---|
| TGGTTCCACG | GGAAGATCTC | GGGCCAGGAG | GCTGTCCAGC | AGCTGCAGCC | TCCCGAGGAT | 60 |
| GGGCTGTTCC | TGGTGCGGGA | GTCCGCGCGC | CACCCCGGCG | ACTACGTCCT | GTGCGTGAGC | 120 |
| TTTGGCCGCG | ACGTCATCCA | CTACCGCGTG | CTGCACCGCG | ACGGCACCT | CACAATCGAT | 180 |
| GAGGCCGTGT | TCTTCTGCAA | CCTCATGGAC | ATGGTGGAGC | ATTAC | | 225 |

(2) INFORMATION FOR SEQ ID NO:8:

(i) SEQUENCE CHARACTERISTICS:
(A) LENGTH: 738 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: human
(B) STRAIN: UT-7

(xi) SEQUENCE DESCRIPTION: SEQ ID NO:8:

| | | | | | |
|---|---|---|---|---|---|
| CAGCATTTGA | CATTGGGAGC | ACAGATCGGA | GAGGGAGAGT | TTGGAGCTGT | CCTGCAGGGT | 60 |
| GAGTACCTGG | GGCAAAAGGT | GGCCGTGAAG | AATATCAAGT | GTGATGTGAC | AGCCCAGGCC | 120 |
| TTCCTGGACG | AGACGGCCGT | CATGACGAAG | ATGCAACACG | AGAACCTGGT | GCGTCTCCTG | 180 |
| GGCGTGATCC | TGCACCAGGG | GCTGTACATT | GTCATGGAGC | ACGTGAGCAA | GGGCAACCTG | 240 |
| GTGAACTTTC | TGCGGACCCG | GGGTCGAGCC | CTCGTGAACA | CCGCTCAGCT | CCTGCAGTTT | 300 |
| TCTCTGCACG | TGGCCGAGGG | CATGGAGTAC | CTGGAGAGCA | AGAAGCTTGT | GCACCGCGAC | 360 |
| CTGGCCGCCC | GCAACATCCT | GGTCTCAGAG | GACCTGGTGG | CCAAGGTCAG | CGACTTTGGC | 420 |
| CTGGCCAAAG | CCGAGCGGAA | GGGGCTAGAC | TCAAGCCGGC | TGCCCGTCAA | GTGGACGGCG | 480 |
| CCCGAGGCTC | TCAAACACGG | GAAGTTCACC | AGCAAGTCGG | ATGTCTGGAG | TTTTGGGGTG | 540 |
| CTGCTCTGGG | AGGTCTTCTC | ATATGGACGG | GCTCCGTACC | CTAAAATGTC | ACTGAAAGAG | 600 |
| GTGTCGGAGG | CCGTGGAGAA | GGGGTACCGC | ATGGAACCCC | CGAGGGCTG | TCCAGGCCCC | 660 |
| GTGCACGTCC | TCATGAGCAG | CTGCTGGGAG | GCAGAGCCCG | CCCGCCGGCC | ACCCTTCCGC | 720 |
| AAACTGGCCG | AGAAGCTG | | | | | 738 |

(2) INFORMATION FOR SEQ ID NO:9:

(i) SEQUENCE CHARACTERISTICS:
(A) LENGTH: 1398 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: human
(B) STRAIN: UT-7

(xi) SEQUENCE DESCRIPTION: SEQ ID NO:9:

-continued

| | | | | | | |
|---|---|---|---|---|---|---|
| ATGCCAACGA | GGCGCTGGGC | CCCGGGCACC | CAGTGTATCA | CCAAATGCGA | GCACACCCGC | 60 |
| CCCAAGCCAG | GGGAGCTGGC | CTTCCGCAAG | GGCGACGTGG | TCACCATCCT | GGAGGCCTGC | 120 |
| GAGAACAAGA | GCTGGTACCG | CGTCAAGCAC | CACACCAGTG | GACAGGAGGG | GCTGCTGGCA | 180 |
| GCTGGGGCGC | TGCGGGAGCG | GGAGGCCCTC | TCCGCAGACC | CCAAGCTCAG | CCTCATGCCG | 240 |
| TGGTTCCACG | GGAAGATCTC | GGGCCAGGAG | GCTGTCCAGC | AGCTGCAGCC | TCCCGAGGAT | 300 |
| GGGCTGTTCC | TGGTGCGGGA | GTCCGCGCGC | CACCCCGGCG | ACTACGTCCT | GTGCGTGAGC | 360 |
| TTTGGCCGCG | ACGTCATCCA | CTACCGCGTG | CTGCACCGCG | ACGGCACCT | CACAATCGAT | 420 |
| GAGGCCGTGT | TCTTCTGCAA | CCTCATGGAC | ATGGTGGAGC | ATTACAGCAA | GGACAAGGGC | 480 |
| GCTATCTGCA | CCAAGCTGGT | GAGACCAAAG | CGGAAACACG | GACCAAGTC | GGCCGAGGAG | 540 |
| GAGCTGGCCA | GGGCGGGCTG | GTTACTGAAC | CTGCAGCATT | TGACATTGGG | AGCACAGATC | 600 |
| GGAGAGGGAG | AGTTTGGAGC | TGTCCTGCAG | GGTGAGTACC | TGGGGCAAAA | GGTGGCCGTG | 660 |
| AAGAATATCA | AGTGTGATGT | GACAGCCCAG | GCCTTCCTGG | ACGAGACGGC | CGTCATGACG | 720 |
| AAGATGCAAC | ACGAGAACCT | GGTGCGTCTC | CTGGGCGTGA | TCCTGCACCA | GGGGCTGTAC | 780 |
| ATTGTCATGG | AGCACGTGAG | CAAGGGCAAC | CTGGTGAACT | TTCTGCGGAC | CCGGGGTCGA | 840 |
| GCCCTCGTGA | ACACCGCTCA | GCTCCTGCAG | TTTTCTCTGC | ACGTGGCCGA | GGGCATGGAG | 900 |
| TACCTGGAGA | GCAAGAAGCT | TGTGCACCGC | GACCTGGCCG | CCCGCAACAT | CCTGGTCTCA | 960 |
| GAGGACCTGG | TGGCCAAGGT | CAGCGACTTT | GGCCTGGCCA | AAGCCGAGCG | GAAGGGGCTA | 1020 |
| GACTCAAGCC | GGCTGCCCGT | CAAGTGGACG | GCGCCCGAGG | CTCTCAAACA | CGGGAAGTTC | 1080 |
| ACCAGCAAGT | CGGATGTCTG | GAGTTTTGGG | GTGCTGCTCT | GGGAGGTCTT | CTCATATGGA | 1140 |
| CGGGCTCCGT | ACCCTAAAAT | GTCACTGAAA | GAGGTGTCGG | AGGCCGTGGA | GAAGGGGTAC | 1200 |
| CGCATGGAAC | CCCCCGAGGG | CTGTCCAGGC | CCCGTGCACG | TCCTCATGAG | CAGCTGCTGG | 1260 |
| GAGGCAGAGC | CCGCCCGCCG | GCCACCCTTC | CGCAAACTGG | CCGAGAAGCT | GGCCCGGGAG | 1320 |
| CTACGCAGTG | CAGGTGCCCC | AGCCTCCGTC | TCAGGGCAGG | ACGCCGACGG | CTCCACCTCG | 1380 |
| CCCCGAAGCC | AGGAGCCC | | | | | 1398 |

(2) INFORMATION FOR SEQ ID NO:10:

(i) SEQUENCE CHARACTERISTICS:
  (A) LENGTH: 1521 base pairs
  (B) TYPE: nucleic acid
  (C) STRANDEDNESS: double
  (D) TOPOLOGY: linear (ii) MOLECULE TYPE: cDNA to mRNA (vi) ORIGINAL SOURCE:
  (A) ORGANISM: human
  (B) STRAIN: UT-7

(xi) SEQUENCE DESCRIPTION: SEQ ID NO:10:

| | | | | | | |
|---|---|---|---|---|---|---|
| ATGGCGGGGC | GAGGCTCTCT | GGTTTCCTGG | CGGGCATTTC | ACGGCTGTGA | TTCTGCTGAG | 60 |
| GAACTTCCCC | GGGTGAGCCC | CCGCTTCCTC | CGAGCCTGGC | ACCCCCTCC | CGTCTCAGCC | 120 |
| AGGATGCCAA | CGAGGCGCTG | GGCCCCGGGC | ACCCAGTGTA | TCACCAAATG | CGAGCACACC | 180 |
| CGCCCCAAGC | CAGGGGAGCT | GGCCTTCCGC | AAGGGCGACG | TGGTCACCAT | CCTGGAGGCC | 240 |
| TGCGAGAACA | AGAGCTGGTA | CCGCGTCAAG | CACCACACCA | GTGGACAGGA | GGGGCTGCTG | 300 |
| GCAGCTGGGG | CGCTGCGGGA | GCGGGAGGCC | CTCTCCGCAG | ACCCCAAGCT | CAGCCTCATG | 360 |
| CCGTGGTTCC | ACGGGAAGAT | CTCGGGCCAG | GAGGCTGTCC | AGCAGCTGCA | GCCTCCCGAG | 420 |

-continued

| | | | | | |
|---|---|---|---|---|---|
| GATGGGCTGT | TCCTGGTGCG | GGAGTCCGCG | CGCCACCCCG | GCGACTACGT | CCTGTGCGTG | 480 |
| AGCTTTGGCC | GCGACGTCAT | CCACTACCGC | GTGCTGGACC | GCGACGGCCA | CCTCACAATC | 540 |
| GATGAGGCCG | TGTTCTTCTG | CAACCTCATG | GACATGGTGG | AGCATTACAG | CAAGGACAAG | 600 |
| GGCGCTATCT | GCACCAAGCT | GGTGAGACCA | AAGCGGAAAC | ACGGGACCAA | GTCGGCCGAG | 660 |
| GAGGAGCTGG | CCAGGGCGGG | CTGGTTACTG | AACCTGCAGC | ATTTGACATT | GGGAGCACAG | 720 |
| ATCGGAGAGG | GAGAGTTTGG | AGCTGTCCTG | CAGGGTGAGT | ACCTGGGGCA | AAAGGTGGCC | 780 |
| GTGAAGAATA | TCAAGTGTGA | TGTGACAGCC | CAGGCCTTCC | TGGACGAGAC | GGCCGTCATG | 840 |
| ACGAAGATGC | AACACGAGAA | CCTGGTGCGT | CTCCTGGGCG | TGATCCTGCA | CCAGGGGCTG | 900 |
| TACATTGTCA | TGGAGCACGT | GAGCAAGGGC | AACCTGGTGA | ACTTTCTGCG | GACCCGGGGT | 960 |
| CGAGCCCTCG | TGAACACCGC | TCAGCTCCTG | CAGTTTTCTC | TGCACGTGGC | CGAGGGCATG | 1020 |
| GAGTACCTGG | AGAGCAAGAA | GCTTGTGCAC | CGCGACCTGG | CCGCCCGCAA | CATCCTGGTC | 1080 |
| TCAGAGGACC | TGGTGGCCAA | GGTCAGCGAC | TTTGGCCTGG | CCAAAGCCGA | GCGGAAGGGG | 1140 |
| CTAGACTCAA | GCCGGCTGCC | CGTCAAGTGG | ACGGCGCCCG | AGGCTCTCAA | ACACGGGAAG | 1200 |
| TTCACCAGCA | AGTCGGATGT | CTGGAGTTTT | GGGGTGCTGC | TCTGGGAGGT | CTTCTCATAT | 1260 |
| GGACGGGCTC | CGTACCCTAA | AATGTCACTG | AAAGAGGTGT | CGGAGGCCGT | GGAGAAGGGG | 1320 |
| TACCGCATGG | AACCCCCCGA | GGGCTGTCCA | GGCCCCGTGC | ACGTCCTCAT | GAGCAGCTGC | 1380 |
| TGGGAGGCAG | AGCCCGCCCG | CCGGCCACCC | TTCCGCAAAC | TGGCCGAGAA | GCTGGCCCGG | 1440 |
| GAGCTACGCA | GTGCAGGTGC | CCCAGCCTCC | GTCTCAGGGC | AGGACGCCGA | CGGCTCCACC | 1500 |
| TCGCCCCGAA | GCCAGGAGCC | C | | | | 1521 |

(2) INFORMATION FOR SEQ ID NO:11:

(i) SEQUENCE CHARACTERISTICS:
        (A) LENGTH: 1942 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human
        (B) STRAIN: UT-7

(xi) SEQUENCE DESCRIPTION: SEQ ID NO:11:

| | | | | | |
|---|---|---|---|---|---|
| CGGAGGCCCT | CCTGGGGGCG | GGCGCGGGGC | GCGGCTCGGG | GGCGCCCCCT | GAGCAGAAAA | 60 |
| CAGGAAGAAC | CAGGCTCGGT | CCAGTGGCAC | CCAGCTCCCT | ACCTCCTGTG | CCAGCCGACT | 120 |
| GGCCTGTGGC | AGGCCATTCC | CAGCGTCCCC | GACTGTGACC | ACTTGCTCAG | TGTGCCTCTC | 180 |
| ACCTGCCTCA | GTTTCCCTCT | GGGGGCGATG | GCGGGGCGAG | GCTCTCTGGT | TTCCTGGCGG | 240 |
| GCATTTCACG | GCTGTGATTC | TGCTGAGGAA | CTTCCCCGGG | TGAGCCCCCG | CTTCCTCCGA | 300 |
| GCCTGGCACC | CCCCTCCCGT | CTCAGCCAGG | ATGCCAACGA | GGCGCTGGGC | CCCGGCACC | 360 |
| CAGTGTATCA | CCAAATGCGA | GCACACCCGC | CCAAGCCAG | GGAGCTGGC | CTTCCGCAAG | 420 |
| GGCGACGTGG | TCACCATCCT | GGAGGCCTGC | GAGAACAAGA | GCTGGTACCG | CGTCAAGCAC | 480 |
| CACACCAGTG | GACAGGAGGG | GCTGCTGGCA | GCTGGGGCGC | TGCGGGAGCG | GGAGGCCCTC | 540 |
| TCCGCAGACC | CCAAGCTCAG | CCTCATGCCG | TGGTTCCACG | GGAAGATCTC | GGGCCAGGAG | 600 |
| GCTGTCCAGC | AGCTGCAGCC | TCCCGAGGAT | GGGCTGTTCC | TGGTGCGGGA | GTCCGCGCGC | 660 |
| CACCCCGGCG | ACTACGTCCT | GTGCGTGAGC | TTTGGCCGCG | ACGTCATCCA | CTACCGCGTG | 720 |
| CTGCACCGCG | ACGGCCACCT | CACAATCGAT | GAGGCCGTGT | TCTTCTGCAA | CCTCATGGAC | 780 |

-continued

| | | | | | | |
|---|---|---|---|---|---|---|
|ATGGTGGAGC|ATTACAGCAA|GGACAAGGGC|GCTATCTGCA|CCAAGCTGGT|GAGACCAAAG|840|
|CGGAAACACG|GGACCAAGTC|GGCCGAGGAG|GAGCTGGCCA|GGGCGGGCTG|GTTACTGAAC|900|
|CTGCAGCATT|TGACATTGGG|AGCACAGATC|GGAGAGGGAG|AGTTTGGAGC|TGTCCTGCAG|960|
|GGTGAGTACC|TGGGGCAAAA|GGTGGCCGTG|AAGAATATCA|AGTGTGATGT|GACAGCCCAG|1020|
|GCCTTCCTGG|ACGAGACGGC|CGTCATGACG|AAGATGCAAC|ACGAGAACCT|GGTGCGTCTC|1080|
|CTGGGCGTGA|TCCTGCACCA|GGGGCTGTAC|ATTGTCATGG|AGCACGTGAG|CAAGGGCAAC|1140|
|CTGGTGAACT|TTCTGCGGAC|CCGGGGTCGA|GCCCTCGTGA|ACACCGCTCA|GCTCCTGCAG|1200|
|TTTTCTCTGC|ACGTGGCCGA|GGGCATGGAG|TACCTGGAGA|GCAAGAAGCT|TGTGCACCGC|1260|
|GACCTGGCCG|CCCGCAACAT|CCTGGTCTCA|GAGGACCTGG|TGGCCAAGGT|CAGCGACTTT|1320|
|GGCCTGGCCA|AAGCCGAGCG|GAAGGGGCTA|GACTCAAGCC|GGCTGCCCGT|CAAGTGGACG|1380|
|GCGCCCGAGG|CTCTCAAACA|CGGGAAGTTC|ACCAGCAAGT|CGGATGTCTG|GAGTTTTGGG|1440|
|GTGCTGCTCT|GGGAGGTCTT|CTCATATGGA|CGGGCTCCGT|ACCCTAAAAT|GTCACTGAAA|1500|
|GAGGTGTCGG|AGGCCGTGGA|GAAGGGGTAC|CGCATGGAAC|CCCCGAGGG|CTGTCCAGGC|1560|
|CCCGTGCACG|TCCTCATGAG|CAGCTGCTGG|GAGGCAGAGC|CCGCCCGCCG|GCCACCCTTC|1620|
|CGCAAACTGG|CCGAGAAGCT|GGCCCGGGAG|CTACGCAGTG|CAGGTGCCCC|AGCCTCCGTC|1680|
|TCAGGGCAGG|ACGCCGACGG|CTCCACCTCG|CCCCGAAGCC|AGGAGCCCTG|ACCCCACCCG|1740|
|GTGGCCCTTG|GCCCCAGAGG|ACCGAGAGAG|TGGAGAGTGC|GGCGTGGGGG|CACTGACCAG|1800|
|GCCCAAGGAG|GGTCCAGGCG|GGCAAGTCAT|CCTCCTGGTG|CCCACAGCAG|GGGCTGGCCC|1860|
|ACGTAGGGGG|CTCTGGGCGG|CCCGTGGACA|CCCCAGACCT|GCGAAGGATG|ATCGCCCGAT|1920|
|AAAGACGGAT|TCTAAGGACT|CT| | | |1942|

TYROSINE KINASE

BACKGROUND OF THE INVENTION

1. Field of the Invention

The present invention relates to a novel tyrosine kinase and a deoxyribonucleic acid (DNA) coding for the same. More particularly, the present invention is concerned with a novel cytoplasmic tyrosine kinase which is increased with respect to expression amount thereof in accordance with the differentiation of blood cells, and is also concerned with a DNA coding for the same. The tyrosine kinase of the present invention can be advantageously used for screening chemical substances having the capability to inhibit or activate the tyrosine kinase activity of at least the tyrosine kinase of the present invention. Therefore, the present invention is also concerned with a method of screening for such chemical substances. The present invention is also concerned with a replicable recombinant DNA molecule comprising a replicable expression vector and, operably inserted in the vector, a DNA coding for the tyrosine kinase of the present invention; a microorganism or animal cell transformed with the replicable recombinant DNA molecule; an antibody reactive with a polypeptide comprising as an immunogen at least part of an amino acid sequence of the tyrosine kinase of the present invention; a sense DNA prepared from the cDNA coding for the tyrosine kinase of the present invention, and an anti-sense DNA which is complementary to the sense DNA; and a sense RNA prepared from the cDNA coding for the tyrosine kinase of the present invention and an anti-sense RNA which is complementary to the sense RNA.

2. Discussion Of Related Art

Human blood contains various types of blood cells, and each of them plays a physiologically important role. For example, erythrocytes carry oxygen in a human body, platelets block bleeding, and leukocytes form an immune system to protect a human body against is infection. These various types of blood cells are derived from hematopoietic stem cells in bone marrow.

Recent studies show that hematopoietic stem cells undergo differentiation into various types of blood cells, osteoclasts, mast cells and the like, when stimulated by various hematopoietic-stimulating factors or various environmental factors. However, the mechanism of the differentiation of hematopoietic stem cells has not yet been fully elucidated. Recent studies also show that a tyrosine kinase greatly participates in the development and differentiation of bodies of animals and insects. It has been considered that a tyrosine kinase does also greatly participate in the differentiation of hematopoietic stem cells. For example, it has been reported that c-kit, which is one of receptor tyrosine kinases, is expressed on the surfaces of hematopoietic stem cells, and functions as a receptor for a hematopoietic growth factor and a mast cell growth factor (see Witte, Cell 63: 5, 1990). This receptor tyrosine kinase controls the differentiation of hematopoietic stem cells.

Tyrosine kinases are enzymes which phosphorylate tyrosine residues of a protein, and the physiologically active sites thereof each consist of about 250 amino acid residues. Tyrosine kinases each have a plurality of well conserved amino acid sequences (see Hanks et al., Science 241: 42, 1988). A tyrosine kinase gene fragment may be obtained by preparing a DNA corresponding to the conserved amino acid sequence and conducting a reverse transcription-polymerase chain reaction (RT-PCR) using the prepared DNA as a primer (see Wilks, Methods in Enzymology 200: 533, 1991).

SUMMARY OF THE INVENTION

It is known that a tyrosine kinase plays an important role in control of transcription and in signal transmission, and that a mutation of the gene coding for a tyrosine kinase, or a viral infection may cause malignant alteration of cells.

Tyrosine kinases are classified into two classes, i.e., those of the receptor type and those of the cytoplasmic type. A cytoplasmic tyrosine kinase has not yet been elucidated as compared to a receptor tyrosine kinase, so that it has been strongly desired to make clear the characteristics of the cytoplasmic tyrosine kinase.

It is an object of the present invention to provide a novel cytoplasmic tyrosine kinase which is considered to control the differentiation of blood cells.

The present inventor has made extensive and intensive studies with a view toward developing a novel cytoplasmic tyrosine kinase. More specifically, the present inventor has conducted a cloning of the gene coding for a tyrosine kinase which participates in the differentiation of human megakaryoblastic leukemia cell line UT-7 (see Komatsu et al,. Cancer Res. 51: 341, 1991) (UT-7 is available from Dr. Norio Komatsu, instructor at the Department of Hematology, Jichi Medical School, Japan), utilizing the RT-PCR method. As a result, the present inventor has unexpectedly found a gene fragment of a novel tyrosine kinase, the mRNA of which is almost not expressed in undifferentiated UT-7, but is increased with respect to expression amount thereof in accordance with the differentiation of UT-7. The present inventor has used this gene fragment as a probe to obtain a cDNA coding for the entire tyrosine kinase from the cDNA library of UT-7, and determined the nucleotide sequence of the obtained cDNA. Further, from the cDNA obtained, the present inventor has prepared anti-sense DNA and RNA, cells transformed with the cDNA, and antibodies reactive with the tyrosine kinase, and conducted screening of chemical substances. Thus, the present invention has been completed.

BRIEF DESCRIPTION OF THE SEQUENCE LISTINGS

In each of SEQ ID NOs. 1 to 5, the left end and right end of the amino acid sequence are the N-terminus and C-terminus, respectively. In each of SEQ ID NOs. 6 to 11, the left end and right end of the nucleotide sequence are the 5'-end and 3'-end, respectively.

SEQ ID NO. 1 is the amino acid sequence of an SH3 domain (which is explained below), which corresponds to the 7th to 70th amino acids in SEQ ID NO. 4 and the 48th to 111th amino acids in SEQ ID NO. 5, wherein both SEQ ID NOs. 4 and 5 are the amino acid sequences of the tyrosine kinase of the present invention.

SEQ ID NO. 2 is the amino acid sequence of an SH2 domain (which is explained below), which corresponds to the 81st to 155th amino acids in SEQ ID NO. 4 and the 122nd to 196th amino acids in SEQ ID NO. 5, wherein both SEQ ID NOs. 4 and 5 are the amino acid sequences of the tyrosine kinase of the present invention.

SEQ ID NO. 3 is the amino acid sequence of a tyrosine kinase domain (which is explained below), which corresponds to the 192nd to 437th amino acids in SEQ ID NO. 4 and the 233rd to 478th amino acids in SEQ ID NO. 5, wherein both SEQ ID NOs. 4 and 5 are the amino acid sequences of the tyrosine kinase of the present invention.

SEQ ID NO. 4 is the amino acid sequence of one region which contains all of the SH3 domain, the SH2 domain and the tyrosine kinase domain. The amino acid sequence of SEQ ID NO. 4 is coded for by the translational region started from the initiation codon at the 331st to 333rd nucleotides of the nucleotide sequence of SEQ ID NO. 11.

SEQ ID NO. 5 is the amino acid sequence of another region which contains all of the SH3 domain, the SH2 domain and the tyrosine kinase domain. The amino acid sequence of SEQ ID NO. 5 is coded for by the translational region started from the initiation codon at the 208th to 210th nucletoides of the nucletoide sequence of SEQ ID NO. 11, and contains the amino acid sequence of SEQ ID NO. 4.

SEQ ID NOs. 6 to 10 are the respective nucleotide sequences of fragments from the nucleotide sequence of SEQ ID NO. 11. The nucleotide sequences of SEQ ID NOs. 6 to 10 are examples of nucleotide sequences coding for the amino acid sequences of SEQ ID NOs. 1 to 5, respectively.

SEQ ID NO. 11 is the entire nucleotide sequence of the cDNA coding for the novel tyrosine kinase of the present invention.

DETAILED DESCRIPTION OF THE INVENTION

In one aspect of the present invention, there is provided an isolated polypeptide having tyrosine kinase activity, comprising an amino acid sequence selected from the group consisting of SEQ ID NOs. 1, 2, 3, 4 and 5. Also, there is provided an isolated deoxyribonucleic acid coding for the polypeptide.

In another aspect of the present invention, there is provided a replicable recombinant DNA molecule comprising a replicable expression vector and, operably inserted in the vector, a deoxyribonucleic acid coding for a polypeptide having tyrosine kinase activity, the polypeptide comprising an amino acid sequence selected from the group consisting of SEQ ID NOs. 1, 2, 3, 4 and 5. Also, there is provided a microorganism or animal cells transformed with the replicable recombinant DNA molecule.

In a further aspect of the present invention, there is provided a method of screening for chemical substances having the capability to inhibit or activate tyrosine kinase activity, which comprises:

contacting a sample material with a polypeptide comprising an amino acid sequence selected from the group consisting of SEQ ID NOs. 1, 2, 3, 4 and 5 to detect a chemical substance having the capability to inhibit or activate the tyrosine kinase activity of at least the polypeptide, wherein the capability of the chemical substances is utilized as a criterion for the detection; and isolating the detected chemical substance from the sample material.

In still a further aspect of the present invention, there is provided an antibody reactive with a polypeptide having tyrosine kinase activity, the polypeptide comprising as an immunogen at least part of an amino acid sequence selected from the group consisting of SEQ ID NOs. 1, 2, 3, 4 and 5.

In still a further aspect of the present invention, there is provided an isolated DNA fragment selected from the group consisting of a sense DNA comprising at least 12 contiguous deoxyribonucleotides of the deoxyribonucleotide sequence of SEQ ID NO. 11, and an anti-sense DNA which is complementary to the sense DNA. Also, there is provided an isolated RNA fragment selected from the group consisting of an anti-sense RNA comprising at least 12 contiguous ribonucleotides of a ribonucleotide sequence complementary to the deoxyribonucleotide sequence of SEQ ID NO. 11, and a sense RNA which is complementary to the anti-sense RNA.

In the present invention, various the term "tyrosine kinase activity" means not only the enzyme activity to phosphorylate a tyrosine residue, but also the activity of the SH2 domain of the tyrosine kinase to recognize a phosphorylated tyrosine residue of other proteins and bind to the residue, and the activity of the SH3 domain of the tyrosine kinase to recognize the amino acid sequence of a proline-rich region of other proteins and bind to the region.

In the present invention, various procedures, such as preparation of a cDNA which is required for cloning, evaluation of the expression of an RNA by northern blotting, screening by hybridization, preparation of a recombinant DNA molecule, determination of a nucleotide sequence of a DNA, and preparation of a cDNA library, can be conducted according to the methods described in standard laboratory manuals. With respect to the illustrative method, reference can be made, for example, to Molecular Cloning, A laboratory manual, edited by Maniatis (1989, Eds., Sambrook, J., Fritsch, E. F., and Maniatis, T., Cold Spring Harbor Laboratory Press).

Preparation of a PCR primer corresponding to the amino acid sequence which is characteristic of tyrosine kinase, and subsequent operation of PCR can be conducted according to the method described in the literature by Wilks (Proc. Natl. Aced. Sci. USA 86: 1603, 1989). Illustratively stated, an oligonucleotide is synthesized by means of a commercially available DNA synthesizer. The synthesized oligonucleotide is purified and then, subjected to PCR, so that the specific region coding for the kinase domain of the tyrosine kinase and having about 210 bp is amplified. The resultant DNA fragment obtained by PCR is isolated, for example, by agarose gel electrophoresis, and the isolated DNA fragment is purified. The purified DNA fragment is subcloned into various vectors, followed by determination of the nucleotide sequence thereof. From the comparison of the determined nucleotide sequence with the nucleotide sequences of the various types of known tyrosine kinases, cloning of the nucleotide fragment of a novel tyrosine kinase can be confirmed.

In order to obtain a clone containing the entire nucleotide sequence coding for the novel tyrosine kinase of the present invention, the nucleotide fragment cloned by the above procedure is isotopically or non-isotopically labeled and, a cDNA library of UT-7 is screened with the labeled nucleotide fragment, for example, by hybridization. Examples of methods for labeling a nucleotide fragment with an isotope include a method in which the terminus of the nucleotide fragment is labeled with [$^{32}$P]γ-ATP using T4 polynucleotide kinase, a nick translation method, and a primer extension method. Alternatively, a clone containing the entire nucleotide sequence coding for the novel tyrosine kinase of the present invention may be obtained by the PCR method, based on the nucleotide sequence of SEQ ID NO. 11.

SEQ ID NO. 11 is a cDNA nucleotide sequence coding for the tyrosine kinase of the present invention. The nucleotide sequence of SEQ ID NO. 11 consists of the 5' non-coding region of 207 nucleotides, the region of 1521 nucleotides coding for the novel tyrosine kinase, and the 3' non-coding region of 214 nucleotides.

SEQ ID NOs. 4 and 5 are the amino acid sequences of the tyrosine kinase of the present invention. Each of the polypeptides of SEQ ID NOs. 4 and 5 contains an SH2 domain, an SH3 domain and a tyrosine kinase domain, which respectively have similar amino acid sequences to the partial amino acid sequences of known cytoplasmic tyrosine kinases [these three types of domains are known to be present in many types of known cytoplasmic tyrosine kinases, e.g., c-src (see Koch et al., Science 252: 668, 1991)]. Further, it has been reported that the SH2 domain and the SH3 domain are also present in signal transmitters, such as phospholipase C-γ, IP3 kinase, and ras-GAP, and that these two types of SH domains play important roles in intracellular signaling pathways (see Pawson and Gish, Cell, 71: 359, 1992). In the tyrosine kinase of the present invention, the SH3 domain has the amino acid sequence of SEQ ID NO. 1, the SH2 domain has the amino acid sequence of SEQ ID NO. 2, and the tyrosine kinase domain has the amino acid sequence of SEQ ID NO. 3. In the amino acid sequence of SEQ ID NO. 4 including the amino acid sequences of the SH3 domain, SH2 domain and tyrosine kinase domain, the SH3 domain corresponds to the 7th to 70th amino acids, the SH2 domain corresponds to the 81st to 155th amino acids, and the tyrosine kinase domain corresponds to the 192nd to 437th amino acids. Further, in the amino acid sequence of SEQ ID NO. 5 also including the amino acid sequences of the SH3 domain, SH2 domain and tyrosine kinase domain, the SH3 domain corresponds to the 48th to 111th amino acids, the SH2 domain corresponds to the 122nd to 196th amino acids, and the tyrosine kinase domain corresponds to the 233rd to 478th amino acids. SEQ ID NO. 6 is an example of the nucleotide sequences of cDNAs coding for the polypeptide having the amino acid sequence of SEQ ID NO. 1. SEQ ID NO. 7 is an example of the nucleotide sequences of cDNAs coding for the polypeptide having the amino acid sequence of SEQ ID NO. 2. SEQ ID NO. 8 is an example of the nucleotide sequences of cDNAs coding for the polypeptide having the amino acid sequence of SEQ ID NO. 3.

It is known that the function of an SH2 domain is to recognize a protein containing a phosphorylated tyrosine residue and bind to the phosphorylated tyrosine residue (see Songyang et al., Cell 72: 767, 1993), and the function of an SH3 domain is to recognize a proline-rich region of exchange factor SOS for a proto-oncogene, such as ras, and bind to the proline-rich region (see Egan et al., Nature 363: 45, 1993). It is considered that these individual SH2 and SH3 domains alone, or a peptide artificially prepared by combining these SH2 and SH3 domains, has a similar function to the function of the SH2 domain or/and the SH3 domain. For evaluating the activity of the tyrosine kinase, it is useful and important to use the following DNA fragments and RNA fragments which are prepared from the respective nucleotide sequences coding for the SH2 domain and the SH3 domain: a sense DNA, an anti-sense DNA, a sense RNA, an anti-sense RNA, or a derivative thereof, such as one which is obtained by methylation, methylphosphorylation, deamination or thiophosphorylation of the above sense DNA, anti-sense DNA, sense RNA or anti-sense RNA.

The amino acid sequence of SEQ ID NO. 5 is highly homologous to that of CSK which is a known cytoplasmic tyrosine kinase having an SH2 domain, an SH3 domain and a kinase domain (with respect to CSK, see Nada et al., Nature 351: 60, 1991). The homology between the amino acid sequence of SEQ ID NO. 5 and the amino acid sequence of CSK is 53.9% with respect to the entire amino acid sequence of tyrosine kinase, 57.4% with respect to the SH2 domain only, 40.5% with respect to the SH3 domain only, and 58.9% with respect to the kinase domain only. CSK has the activity to specifically phosphorylate the C-terminal tyrosine residues of expression products of src family genes to thereby suppress activation of the expression products of the src family genes. Recent study of mice deficient in CSK gene, which are generated by gene targeting, shows that, when the expression products of src family genes are constantly activated in mice, all mice die at their early embryonic stages, due to defects in the formation of neural tubes (see Imamoto & Soriano, Cell 73: 1117, 1993; and Noda et al., Cell 73: 1125, 1993). Expression of the CSK gene is found in various organs. However, in view of the fact that the expression of the gene coding for the tyrosine kinase of the present invention is found only in brain cells and only at the early differentiation stage of blood cells (see Example 8 below), the tyrosine kinase of the present invention appears to play a physiologically different role from the role of CSK.

Tyrosine kinases can generally phosphorylate the tyrosine residues of an enolase protein and a synthetic peptide as substrates, both of which have a tyrosine-rich sequence. However, with respect to substrates upon which tyrosine kinases act in cells, there are different substrates specific for respective tyrosine kinases. Therefore, it is considered that a substrate for the novel tyrosine kinase of the present invention is also specific and different from the substrates for the conventionally known tyrosine kinases. Further, recent study on an SH3 domain and an SH2 domain using a synthetic peptide library containing phosphorylated tyrosines shows that the SH3 domain and the SH2 domain individually, specifically recognize certain amino acid sequences and bind to them. Therefore, it is considered that not only the entire region of the tyrosine kinase of the present invention, but also the SH3 domain, the SH2 domain and the tyrosine kinase domain thereof have respective specific substrates and binding proteins therefor, which are different from those for the conventionally known tyrosine kinases.

It is known that an mRNA having a plurality of initiation codons (AUG) may be translated into various polypeptide fragments despite a fixed nucleotide sequence thereof, as mentioned in general remarks of the literature by M. Kozak (J. Cell Biol. 115: 887, 1991). In the present invention, the cDNA of SEQ ID NO. 11 has two initiation codons respectively at a position of the 208th to 210th nucleotides and at a position of the 331st to 333rd nucleotides, so that two different polypeptide fragments shown in SEQ ID NOs. 5 and 4 can be obtained by expression of the cDNA. SEQ ID NO. 9 is an example of cDNA sequences coding for a polypeptide having the amino acid sequence of SEQ ID NO. 4. SEQ ID NO. 10 is an example of cDNA sequences coding for a polypeptide having the amino acid sequence of SEQ ID NO. 5.

In the present invention, respective homologous variants of the polypeptides having the amino acid sequences of SEQ ID NOs. 4 and 5 can be prepared by standard methods without impairing tyrosine kinase activity.

In the present invention, the respective DNAs coding for the polypeptides having the amino acid sequences of SEQ ID NOs. 4 and 5, and the DNA of SEQ ID NO. 11, can take various forms, such as a cDNA, a chromosomal DNA having introns and exons, and an artificial DNA which is obtained by ligating, to the cDNA or chromsomal DNA, synthesized oligonucleotides prepared by a known DNA synthesis method. It is known that, by the degeneracy of the genetic code, a certain polypeptide can be coded for by different nucleotide sequences. It is also known that the 5' non-coding region and the 3' non-coding region of a DNA do not participate in formation of the amino acid sequence of a polypeptide coded for by the DNA, so that these non-coding regions are likely to undergo mutation.

As is apparent from Example 8 described below, the amount of mRNA of the gene coding for the tyrosine kinase of the present invention is small in undifferentiated UT-7, but is increased in accordance with the differentiation of UT-7 into megakaryocyte or erythroblast. Therefore, it is considered that the tyrosine kinase of the present invention plays an important role in the differentiation of blood cells.

As a method of preparing a replicable recombinant DNA molecule comprising a replicable expression vector and, operably inserted in the vector, a part or whole of the DNA coding for the tyrosine kinase of the present invention, and as a method of transforming a microorganism or animal cells with the above replicable recombinant DNA molecule, reference can be made, for example, to the methods in Example 10 described below. The microorganisms or animal cells transformed with a gene coding for the tyrosine kinase of the present invention can be utilized in fundamental studies of tyrosine kinases, studies of drug design, and development of pharmaceuticals. Examples of such pharmaceuticals include a carcinostatic agent which specifically controls a signal transmission system mediated by the tyrosine kinase, and an agent for controlling the differentiation of blood cells.

The anti-sense DNA and the anti-sense RNA of the present invention, which are prepared utilizing a part of the nucleotide sequence of SEQ ID NO. 11, can be used in studies of the differentiation of blood cells, and development of pharmaceuticals, such as an agent for controlling the differentiation of blood cells. It is also possible to regulate gene expression in cells by use of a DNA fragment or an RNA fragment, which is complementary to or corresponding to at least a part of the nucleotide sequence of SEQ ID NO. 11, such as a sense DNA, an anti-sense DNA, a sense RNA, an anti-sense RNA, or a derivative thereof which is obtained by methylation, methylphosphorylation, deamination or thiophosphorylation of the sense DNA, anti-sense DNA, sense RNA or anti-sense RNA. As is shown in Example 8 below, the anti-sense DNA has the ability to specifically bind to the mRNA of the gene coding for the tyrosine kinase of the present invention and, therefore, the anti-sense DNA can be advantageously used for detecting the expression of the tyrosine kinase gene of the present invention. In addition, as is shown in Example 9 below, the anti-sense RNA can also be advantageously used in a likewise manner for detecting the expression of the tyrosine kinase gene of the present invention. The size of each of the sense DNA, the anti-sense DNA, the sense RNA, the anti-sense RNA and the derivatives thereof is at least 12 mer, preferably 14 mer to 16 mer.

Example 11 (which is described below) shows an example of methods of preparing an antibody using a polypeptide comprising as an immunogen at least part of an amino acid sequence of the tyrosine kinase of the present invention. The prepared antibody can be advantageously used for various purposes, such as detection of the tyrosine kinase of the present invention.

According to the present invention, a chemical substance having the capability to inhibit or activate the tyrosine kinase activity defined above can be obtained by screening, utilizing the above-mentioned capability as a criterion. More specifically, it is possible to screen a chemical substance having the capability to inhibit or activate the tyrosine kinase activity of at least the tyrosine kinase of the present invention, utilizing the above-mentioned capability as a criterion. It is also possible to obtain a chemical substance having the capability to regulate the intracellular signal transmission mediated by the tyrosine kinase of the present invention by screening, wherein inhibition of the functions of the SH2 domain and the SH3 domain of the tyrosine kinase of the present invention to recognize and bind to their respective recognition sites is utilized as a criterion for the detection (as mentioned above, SH2 specifically recognizes a phosphorylated tyrosine residue of a protein, and SH3 specifically recognizes the proline-rich region of exchange factor SOS for a proto-oncogene, such as ras). For example, as shown in Example 13 below, erbstatin having the capability to inhibit tyrosine kinase activity (with respect to erbstatin, see Umezawa et al., J. Antibiot. 39: 170, 1986) can be detected and isolated by screening, wherein inhibition of tyrosine kinase activity is utilized as a criterion for the detection. It is expected that a novel substance would be able to be isolated by this method. This method can also be utilized for development of useful pharmaceuticals, such as a carcinostatic agent, and an agent for inhibiting or promoting the proliferation of a cell.

The cDNA coding for the tyrosine kinase of the present invention can be obtained from cell lines other than UT-7, such as human peripheral blood mononuclear cells (such as T cells and NK cells), human acute myelogenous leukemia cell line KGla (see Blood 62: 709, 1983), cell line KMT-2 established from human umbilical cord blood (see Blood 76: 501, 1990), and human chronic myelogenous leukemia cell line K562 (see Blood 45: 321, 1975) (ATCC accession No. CCL243), in substantially the same manner as in Examples 1 to 7.

BEST MODE FOR CARRYING OUT THE INVENTION

Hereinbelow, the present invention will be illustrated with reference to Examples, which however should not be construed as limiting the scope of the present invention.

EXAMPLE 1

[Preparation of a poly(A)$^+$RNA of human blood cell line UT-7]

Cell line UT-7 (Komatsu et al., Cancer Res. 51: 341, 1991) (UT-7 is available from Dr. Norio Komatsu, instructor at the Department of Hematology, Jichi Medical School, Japan) is cultured and passaged by a method in which human granulocyte monocyte colony-stimulating factor (hGM-CSF) is added to Iscove's modified Dulbecco's medium (IMDM) containing 10% fetal calf serum (FCS) so that the concentration of hGM-CSF becomes 2 ng/ml, and UT-7 cells are inoculated in the resultant culture medium and incubated at 37° C. in a $CO_2$ incubator. Cultured UT-7 cells are obtained.

The differentiation of UT-7 cells into megakaryocites are conducted in the following manner. The cultured UT-7 cells in the culture medium are diluted with the same culture medium so that the concentration of the cells becomes $2\times10^5$ cells/ml. Then, hGM-CSF is added to the resultant diluted cells so that the concentration of hGM-CSF becomes 2 ng/ml, and Phorbol 12-Myristate 13-Acetate (PMA) is added thereto so that the concentration of PMA becomes 10 ng/ml. Then, the cells are incubated for 3 days, and the resultant megakaryocytes are recovered.

On the other hand, the differentiation of UT-7 cells into erythroblasts are conducted in the following manner. The cultured UT-7 cells in the culture medium are diluted with the same culture medium so that the concentration of the cells becomes $2\times10^5$ cells/ml. Human erythropoietin (hEPO) is added to the resultant diluted cells so that the concentration of hEPO becomes 1 Unit/ml, and butyric acid is added thereto so that the concentration of n-butyric acid becomes 1.3 mM. Then, the cells are incubated for 3 days, and the resultant erythroblasts are recovered.

With respect to each of these three types of cells, i.e., cells of unstimulated UT-7, megakaryocytes and erythroblasts, $1\times10^8$ cells are collected and washed three times with PBS (−), and are used for the extraction of RNA in the following manner.

From the collected cells, total RNA is extracted by Lithium Chloride/Urea method (Eur. J. Biochem. 107: 303, 1980). Then, a poly (A)⁺RNA is isolated and purified from the total RNA by using Oligotex-dT 30 (manufactured and sold by Takara Shuzo Co., Ltd., Japan).

EXAMPLE 2

[Construction of a primer specific for tyrosine kinase gene]

PCR is conducted according to the method of Wilks (Proc. Natl. Acad. Sci. USA 86: 1603, 1989), wherein use is made of two types of mixed primers respectively having sequences complementary to subdomains 7 and 9 of tyrosine kinase, and having their respective restriction sites ligated therein, that is, sense primer PTKI: 5'-TTGTCGACAC(AC)G(AG)GA(CT)(CT)T(CG)GC(ACGT)GC(ACGT)(AC)G-3' (27-mer having SalI site as a restriction site), and anti-sense primer PTKII:3'-CT(AG)CA(CG)ACC(AT)(CG)(AG)A(AT)ACCTTAAGGT-5' (24-mer having EcoRI site as a restriction site), as follows.

A synthetic oligonucleotide is constructed by means of an automatic DNA synthesizer using a solid phase method. As the automatic DNA synthesizer, 391PCR-MATE (manufactured and sold by APPLIED BIOSYSTEMS, INC., U.S.A.) is used. Nucleotides, a carrier having 3'-nucleotide supported thereby, a solution, and a reagent are used in accordance with the manual accompanying the synthesizer. A coupling reaction is conducted to synthesize an oligonucleotide in a state supported by a carrier. A protecting group at the 5' terminus of the oligonucleotide is removed by applying trichloroacetic acid to the oligonucleotide, and the oligonucleotide is placed in a concentrated ammonia solution and allowed to stand at room temperature for 1 hour, thereby liberating the oligonucleotide from the carrier. Subsequently, the concentrated ammonia solution containing the oligonucleotide liberated from the carrier is allowed to stand at 55° C. for more than 14 hours in a sealed vial, to thereby remove the protecting groups from both the nucleic acid and phosphate of the oligonucleotide. The obtained oligonucleotide, from which the carrier and protecting groups have been removed, is purified by means of an OPC cartridge (manufactured and sold by APPLIED BIOSYSTEMS, INC., U.S.A.), and detritylated using 2% trifluoroacetic acid, thereby obtaining a purified primer. The purified primer is dissolved in deionized water so that the concentration of the primer becomes 1 µg/µl, and the obtained solution is used in the PCR described below.

EXAMPLE 3

[Synthesis of a cDNA]

A cDNA is synthesized utilizing the poly(A)⁺RNA obtained in Example 1. Specifically, 2 µg of the poly(A)⁺RNA is dissolved in 12.3 µl of deionized water, thereby obtaining a solution. To the obtained solution are added 2 µl of 10× buffer [containing 500 mM KCl, 100 mM Tris-HCl (pH 8.3), 15 mM MgCl$_2$, and 0.01% gelatin], 4 µl of dNTP (2.5 mM), 1 µl of the above-mentioned anti-sense primer PTKII (1 µg/µl) specific for tyrosine kinase, 0.2 µl of avian myeloblastosis virus reverse transcriptase (manufactured and sold by Life Science Laboratories, U.S.A: 32 U/µl), and 0.5 µl of RNase inhibitor (manufactured and sold by Boehringer-Mannheim GmbH, Germany: 40 U/µl). The resultant mixture is allowed to stand at 37° C. for 75 minutes, and further allowed to stand at 65° C. for 10 minutes.

EXAMPLE 4

[PCR using primers specific for the tyrosine kinase gene]

Amplification of the cDNA by PCR is conducted as follows. To 20 µl of the cDNA solution obtained in Example 3 are added 8 µl of 10× buffer [containing 500 mM KCl, 100 mM Tris-HCl (pH 8.3), 15 mM MgCl$_2$, and 0.01% gelatin], 6.4 µl of dNTP (2.5 mM), 1.5 µl of the above-mentioned sense primer PTKI (1 µg/µl) specific for tyrosine kinase, and 0.2 µl of Taq DNA polymerase (AmpliTaq: manufactured and sold by Perkin Elmer Cetus Co., Ltd., U.S.A.: 5 U/µl). To the resultant mixture, deionized water is added so that the total volume becomes 100 µl. PCR procedure is conducted first at 94° C. for 1 minute, next at 37° C. for 2 minutes, and then at 72° C. for 3 minutes. This procedure is repeated 40 times and then, the reaction mixture is allowed to stand at 72° C. for 7 minutes. A portion of the resultant PCR product is electrophoresed in 2% agarose gel. Subsequently, the gel is then stained with ethidium bromide and observed under ultraviolet light, to thereby confirm that a cDNA having about 210 bp nucleotides has been amplified.

EXAMPLE 5

[Cloning and sequencing of the PCR product]

A whole amount of the remaining PCR product is electrophoresed in 2% agarose gel composed of low melting point agarose. Subsequently, the gel is stained with ethidium bromide, and a band corresponding to about 210 bp is confirmed under ultraviolet light, and a gel portion having the band containing cDNA is cut out. The thus obtained cDNA is purified from the gel. The purified cDNA is digested with restriction enzymes EcoRI and SalI, and a portion of the digested cDNA is electrophoresed in agarose gel to obtain a cDNA fragment which is to be inserted into a vector.

As a vector, pBluescript II KS (manufactured and sold by Toyobo Co., Ltd., Japan) is employed. Before introducing the above prepared cDNA fragment into the vector, the vector is digested with restriction enzymes EcoRI and SalI, and termini of the digested vector are dephosphorylated with alkaline phosphatase (CIAP: manufactured and sold by Takara Shuzo Co., Ltd., Japan). The obtained digested vector and the above-mentioned cDNA are mixed with each other in a molar ratio of 1:5, and the cDNA is ligated into the vector by using T4 ligase (manufactured and sold by New England Bio Labs, U.S.A.). The resultant vector pBluescript having the cDNA inserted therein is introduced into *E. coli* strain JM109, and the strain is seeded on a plate of semi-solid L-broth medium containing 50 µg/ml of ampicillin, and allowed to stand at 37° C. for 12 hours. From colonies which have appeared, colonies are selected at random, and digested with restriction enzymes EcoRI and SalI to thereby confirm that a cDNA having about 210 bp can be cut out by the digestion. Thus, it is confirmed that the desired cDNA has been introduced in the selected clones. The nucleotide sequence of the cDNA of each of the confirmed clones is determined by means of fluorescence sequencer model 373A (manufactured by APPLIED BIOSYSTEMS, INC., U.S.A.). As a result, it is found that, with respect to the clones having the cDNA prepared using the poly(A)+RNA derived from the unstimulated UT-7 cells, the tyrosine kinase gene of the present invention is detected from only 1 clone among 98 clones; with respect to the clones having the cDNA prepared using the poly(A)⁺RNA derived from the megakaryocytes differentiated from the UT-7 cells, the tyrosine kinase gene of the present invention is detected from 8 clones among 51 clones; and with respect to the clones having the cDNA prepared using the poly(A)⁺RNA derived from the erythroblasts differentiated from the UT-7 cells, the tyrosine kinase gene of the present invention is detected from 7 clones among 53 clones. This indicates that the tyrosine kinase gene of the present invention does far more frequently occur in differentiated cells than in undifferentiated cells. This gene of the present invention corresponds to the 1276th to 1421st nucleotides of the nucleotide sequence of SEQ ID NO. 11.

EXAMPLE 6

[Preparation of a cDNA library, and cloning of the entire region of the tyrosine kinase gene of the present invention]

Using the poly(A)$^+$RNA of the unstimulated UT-7 cells which has been isolated and purified according to the above-described method, a cDNA library is prepared. For the preparation of a cDNA library, pCDM8 vector cDNA library construction kit (manufactured and sold by Invitrogen, Netherlands) is used in accordance with the manual accompanying the kit.

Next, by using colony hybridization method, a cDNA clone coding for the entire region of the tyrosine kinase gene of the present invention is searched from colonies containing about 5×10$^5$ cells in the cDNA library prepared above. The hybridization is conducted in the following manner. The colonies of cells are transferred to a nylon filter (Hybond N+: manufactured and sold by Amersham International, U.K.). The nylon filter having the cells thereon is treated with alkali (by leaving the nylon filter for 7 minutes on a filter paper which contains, absorbed therein, 1.5M NaCl and 0.5M NaOH), neutralized (by leaving the nylon filter for 3 minutes on a filter paper which contains, absorbed therein, 1.5M NaCl, 0.5M Tris-HCl pH 7.2, and 1 mM EDTA) twice, washed by shaking for 5 minutes in SSPE of 2-fold concentration (0.36M NaCl, 0.02M sodium phosphate pH 7.7, 2 mM EDTA), and air dried. Then, the thus treated nylon filter is left for 20 minutes on a filter paper which contains 0.4M NaOH absorbed therein, washed by shaking for 5 minutes in SSPE of 5-fold concentration, and air dried. The dried filter is subjected to screening by using a cDNA probe labeled with radioisotope $^{32}$P The screening is conducted in the following manner.

A cDNA probe labeled with radioisotope $^{32}$P is prepared as follows. The pBluescript having, inserted therein, the cDNA fragment coding for the tyrosine kinase of the present invention, which is obtained in Example 5, is digested with restriction enzymes SalI and EcoRI, to thereby cut out the cDNA fragment, and electrophoresed in low melting point agarose. Then, the cDNA fragment is separated and purified from the gel, and the purified cDNA fragment is labeled by means of a DNA labeling kit (Megaprime DNA labeling system: manufactured and sold by Amersham International, U.K.). Specifically, the labeling is conducted as follows. To 25 ng of the DNA fragment are added 5 μl of a primer solution and deionized water so that the total volume becomes 33 μl, and the resultant mixture is heated in a boiling water bath for 5 minutes. To the mixture are then added 10 μl of a reaction buffer containing dNTP, 5 μl of α-$^{32}$P-dCTP, and 2 μl of a DNA polymerase solution, and the resultant mixture is heated in a water bath at 37° C. for 10 minutes. From the heated mixture, the DNA is purified using Sephadex column (Quick Spin Column Sephadex G-50: manufactured and sold by Boehringer-Mannheim GmbH, Germany). The purified DNA is heated in a boiling water bath for 5 minutes, and cooled in an ice bath for 2 minutes.

The above-mentioned nylon filter carrying cells to be screened is immersed in a prehybridization solution composed of SSPE of a 5-fold concentration, a Denhardt's solution of a 5-fold concentration, 0.5% SDS (sodium dodecyl sulfate), and 10 mg/ml of salmon sperm DNA denatured in a boiling water bath, wherein the concentration of each component is a final concentration as determined in the prehybridization solution. The filter in the prehybridization solution is shaken at 65° C. for 2 hours. Hybridization is conducted by shaking the filter at 65° C. for 16 hours in a hybridization solution which has the same composition as that of the above-mentioned prehybridization solution except that it additionally contains the above-obtained $^{32}$P-labeled cDNA probe.

The filter is then washed twice by immersing it with shaking in an SSPE solution containing 0.1% SDS at 65° C., and further washed 4 times at 65° C. in a solution obtained by 10-fold diluting an SSPE solution containing 0.1% SDS with water. The washed filter is subjected to autoradiography by use of a sensitized screen. Clones are picked up from a strongly luminous colony, and seeded again to thereby grow colonies, and a screening is conducted in the same manner as described above, thereby obtaining a desired clone.

According to the method described in the above-mentioned laboratory manual by Maniatis et al., plasmid pCDM8 is purified from the obtained clones. The purified plasmid is digested with restriction enzyme XhoI to thereby obtain a cDNA. The cDNA is purified by electrophoresis in low melting point agarose, and the purified cDNA is inserted into plasmid pBluescript. The nucleotide length of the purified cDNA is about 2 kbp.

EXAMPLE 7

[Determination of the nucleotide sequence of the tyrosine kinase gene of the present invention]

The cDNA coding for the tyrosine kinase of the present invention obtained in Example 6 is sequenced using ALFDNA sequencer (manufactured and sold by Pharmacia Fine Chemicals AB, Sweden) and labeling kit for ALF sequencer (which labeling kit is manufactured and sold by Pharmacia Fine Chemicals AB, Sweden) according to the manuals accompanying the sequencer and the kit. Specifically, a deletion mutant is prepared, using a deletion mutant kit for kilosequence (manufactured and sold by Takara Shuzo Co., Ltd., Japan), according to the manual accompanying the kit. Using the deletion mutant, the entire nucleotide sequence of the cDNA coding for the tyrosine kinase of the present invention is determined in both directions.

EXAMPLE 8

[Detection of production of the mRNA, which codes for the tyrosine kinase of the present invention, in various types of tissue cells by northern blotting]

For detection of the mRNA coding for the tyrosine kinase of the present invention in human tissue cells and blood cells, the following filters are used: commercially available filters carrying mRNAs of various types of tissue cells, specifically, Human Multiple Tissue Northern Blot, Human Multiple Tissue Northern Blot II, Human Fetal Multiple Tissue Northern Blot, and Human Brain Multiple Tissue Northern Blot (all manufactured and sold by Clontech, U.S.A.), and a filter prepared by a method in which the mRNA obtained by the method shown in Example 1 is electrophoresed in agarose gel and transferred to Zeta-Prob (manufactured and sold by Bio-Rad laboratories, U.S.A.). First, the cDNA coding for the entire region of the tyrosine kinase of the present invention is digested with SmaI, thereby obtaining a fragment of about 800 bp. The obtained fragment is labeled with $^{32}$P by use of the above-mentioned DNA labeling kit (MegaPrime DNA labeling system, manufactured and sold by Amersham International, U.K.), and the labeled fragment is reacted with the mRNAs carried by the above-mentioned filters, to thereby examine the presence or absence of mRNA coding for the tyrosine kinase of the present invention.

As a result, it has been found that, with respect to tissue cells of an adult human, the mRNA coding for the tyrosine kinase of the present invention is not detected in the total mRNA of the cells of heart, placenta, liver, skeletal muscle, kidney, pancreas, prostate, testis, ovary and small intestine. Whereas, it has been found that the mRNA coding for the tyrosine kinase of the present invention is detected in the total mRNA of the cells of brain, spleen, colon, and in the total mRNA of peripheral blood lymphocytes. It has also been found that, in the total mRNA of lung and thymus cells, the mRNA coding for the tyrosine kinase of the present invention is detected, although the amount of the mRNA is small. On the other hand, it has been found that, with respect to tissue cells of a human fetus, the mRNA coding for the tyrosine kinase of the present invention is not detected in the total mRNA of the cells of heart, lung, liver and kidney, but detected in the total mRNA of the cells of brain. Regarding adult human brain tissue cells, the mRNA coding for the tyrosine kinase of the present invention is detected in the total mRNA of the cells of amygdala, caudate nucleus, corpus callosum, hippocampus, hypothalamus, substantia nigra, subthalamic nucleus, and thalamus.

The mRNA coding for the tyrosine kinase of the present invention is detected also in the total mRNAs respectively of human acute myelogenous leukemia cell line KG1a (see Blood 62: 709, 1983), cell line KMT-2 established from human umbilical cord blood (see Blood 76: 501, 1990), human chronic myelogenous leukemia cell line K562 (see Blood 45: 321, 1975) (ATCC accession No. CCL243), and the above-mentioned myelogenous megakaryoblastic leukemia cell line UT-7. Further, it has been found that, with respect to cell lines K562 and UT-7, the amount of the mRNA coding for the tyrosine kinase of the present invention is increased when they are induced to differentiate into megakaryocytes by stimulation with PMA.

Therefore, it is considered that the mRNA coding for the tyrosine kinase of the present invention is specifically produced in brain cells and blood cells, and that the production of this mRNA in blood cells is increased in accordance with the differentiation of the blood cells.

The mRNA coding for the tyrosine kinase of the present invention is not detected in lymphocytic cells, such as hepatocellular carcinoma cell line Hep3B (Nature 282: 615, 1979), fetal pulmonary fibroblast line MRC-5 (Nature 227: 168, 1970), and acute lymphocytic leukemia cell line MOLT-4 (J. Nat. Cancer Inst. 49: 891, 1972).

EXAMPLE 9

[Detection of production of the mRNA, which codes for the tyrosine kinase of the present invention, in peripheral blood cells by in situ hybridization technique]

The mRNA coding for the tyrosine kinase of the present invention in peripheral blood lymphocytes is detected as follows. Mononuclear cells are isolated from adult human peripheral blood by use of Ficoll-Paque (trade mark) (manufactured and sold by Pharmacia Fine Chemicals AB, Sweden). The isolated mononuclear cells are fixed onto a slide glass by means of Cytospin 3 (manufactured and sold by Shandon inc., U.K.). The mononuclear cells are subjected to fixation-treatment for 15 minutes with 4% paraformaldehyde PBS. Subsequently, the slide glass having the cells fixed thereto is immersed for 15 minutes in a solution containing 10 mM Tris-HCl (pH 8.0), 1 mM EDTA, and 10 µg/ml pronase K. The cells fixed to the slide glass are further subject to fixation-treatment for 15 minutes with 4% paraformaldehyde PBS, washed once with PBS, immersed in 0.2M HCl for 10 minutes, washed once with PBS, and immersed in 0.1M triethanolamine-HCl (pH 8.0) for 1 minute. Subsequently, the cells are immersed for 10 minutes in a solution containing 0.1M triethanolamine-HCl (pH 8.0) and 0.25% acetaldehyde, and washed with PBS. Then, the cells are successively immersed in 70% ethanol for 15 seconds, 80% ethanol for 15 seconds, 90% ethanol for 15 seconds, and 100% ethanol for 15 seconds, to thereby dehydrate the cells completely. Then, the dehydrated cells are air dried. All of the above-mentioned treating solutions are those which have been cooled to 4° C. before use. The cells fixed by the above operation are used for the in situ hybridization, which is described below.

A digoxigenin-labeled RNA probe for use in the in situ hybridization is prepared in the following manner. A SmaI fragment of the cDNA coding for the entire region of the tyrosine kinase of the present invention, which is the same fragment as used in the northern blotting in Example 8, is ligated into the SmaI site of pBluescript having dephosphorylated termini, to thereby obtain a vector for in situ hybridization. The obtained vector is purified using a plasmid purification column (manufactured and sold by QUIAGEN, Germany), and digested with restriction enzymes BamHI and EcoRI. From nucleotide fragments obtained by the digestion, an anti-sense RNA probe and a sense RNA probe (as a control) for detecting the mRNA coding for the tyrosine kinase of the present invention are prepared using T3 or T7 RNA polymerase, and DIG RNA labeling kit (manufactured and sold by Boehringer-Mannheim GmbH, Germany) according to the manual accompanying the kit. These probes are used for the detection of the mRNA coding for the tyrosine kinase of the present invention in peripheral blood mononuclear cells.

A hybridization solution [containing 50% formamide, 10 mM Tris-HCl (pH 7.6), 200 µg/ml of tRNA, 1-fold Denhardt's solution, 10% dextran sulfate, 600 mM NaCl, 0.25% SDS, and 1 mM EDTA (pH 8.0)] is heated to and kept at 85° C. for 10 minutes. The sense RNA probes and the anti-sense RNA probes are individually added to the heated solution so that the concentration of each of the RNA probes becomes 10 µg/ml, and each of the resultant mixtures is further kept at 85° C. for 3 minutes, to thereby denature the RNA probes. The resultant hybridization solutions containing the denatured RNA probes are individually, dropwise added to the above-mentioned air-dried cells on the slide glass. The cells are covered with Parafilm and allowed to stand at 50° C. for 16 hours to thereby conduct a hybridization.

After completion of the hybridization, the cells on the slide glass are immersed in 5× SSC at 50° C. to thereby remove the Parafilm from the cells, and then immersed in a mixture of 2× SSC and 50% formamide at 60° C. for 30 minutes. Then, the cells are immersed in a solution containing 10 mM Tris-HCl (pH 7.6), 500 mM NaCl and 1 mM EDTA at 37° C. for 10 minutes, immersed in a solution at 37° C. for 30 minutes, which solution has been prepared by adding RNase A to the same solution as mentioned above so that the concentration of RNase A becomes 20 µg/ml, and further immersed in the same solution as mentioned above, which does not contain RNase A, at 37° C. for 10 minutes. Then, the cells are immersed in 2× SSC at 50° C. for 20 minutes, and further immersed in 0.2× SSC at 50° C. for 20 minutes twice, to thereby wash the cells.

Cells containing the mRNA coding for the tyrosine kinase of the present invention are stained using a DIG nucleic acid assay kit containing an alkaline phosphatase-labeled DIG antibody (manufactured and sold by Boehringer-Mannheim GmbH, Germany) according to the manual accompanying the kit. Further, the cells are also stained with hematoxylin to thereby morphologically identify the cells containing the mRNA. As a result, it is confirmed that the mRNA coding for the tyrosine kinase of the present invention is produced in a large amount in lymphocytic cells.

In order to more specifically identify the lymphocytic cells containing the mRNA coding for the tyrosine kinase of the present invention, human peripheral blood mononuclear cells are stained, individually using FITC-labeled anti-CD3 antibody (Leu 4, manufactured and sold by BECTON DICKINSON AND COMPANY, U.S.A.), FITC-labeled anti-CD19 antibody (Leu 12, manufactured and sold by BECTON DICKINSON AND COMPANY, U.S.A.), and FITC-labeled anti-CD56 antibody (Leu 19, manufactured and sold by BECTON DICKINSON AND COMPANY, U.S.A.), which antibodies are able to specifically react with a T cell, a B cell and an NK cell, respectively. The stained mononuclear cells are classified into 3 groups by use of flow cytometer EPICS Elite (manufactured and sold by Coulter corp., U.K.), according to the type of antibody with which the cells have reacted. With respect to the 3 groups of cells, the presence or absence of the mRNA coding for the tyrosine kinase of the present invention is examined by the method described above. As a result, it is found that about 5% to 20% of the cells which have reacted with anti-CD3 antibody, and about 30% to 70% of the cells which have reacted with anti-CD56 antibody contain the mRNA coding for the tyrosine kinase of the present invention, whereas almost all of the cells which have reacted with anti-CD19 antibody do not contain the mRNA coding for the tyrosine kinase of the present invention. These results clearly show that the tyrosine kinase of the present invention plays an important role in the differentiation, proliferation and functioning of T cells and NK cells.

EXAMPLE 10
[Preparation of a transformant cell strain having the tyrosine kinase gene of the present invention introduced therein]

DNAs respectively having the sequences of SEQ ID NOs. 9 and 10 are individually synthesized by the PCR method, based on the nucleotide sequence of SEQ ID NO. 11, i.e., the tyrosine kinase gene of the present invention. An early promoter of SV 40 virus is ligated upstream of each of the synthesized DNAs, and a termination codon (TGA in DNA sequence), a poly (A)$^+$ signal of SV 40 virus and the dihydrofolic acid reductase gene are ligated, in this order, downstream of each of the synthesized DNAs, to thereby prepare expression plasmid vectors for use in production of polypeptides comprising the amino acid sequences of SEQ ID NOs. 4 and 5, respectively.

Each of the prepared plasmids is purified. 20 μg of each of the purified plasmids is individually introduced to CHO cells suspended in a glucose solution. Introduction of the plasmids into the CHO cells is conducted by applying 600 V electricity to the cell suspension, using a gene pulser (manufactured and sold by Bio-Rad laboratories, U.S.A.). The thus treated CHO cells are cultured in a medium containing 10% fetal calf serum for 2 days. Then, the CHO cells are further cultured in a medium [Dulbecco's MEM containing 10% dialyzed fetal calf serum and methotrexate (MTX)], to thereby select cells which have been transformed. mRNA is extracted from the selected cells, and poly(A)$^+$RNA is isolated from the mRNA by use of an oligo dT gel column. A filter for use in northern blotting is prepared by utilizing the poly(A)$^+$RNA according to the method shown in Example 8. Using the filter, northern blotting is conducted in the same manner as in Example 8 to thereby confirm the presence of the mRNA coding for the tyrosine kinase of the present invention. As a result, it is confirmed that the transformant cells capable of producing the tyrosine kinase of the present invention is obtained.

DNAs respectively having the sequences of SEQ ID NOs. 6, 7 and 8 are individually prepared by utilizing the PCR method. Each of the prepared DNAs is individually ligated to restriction site SmaI of an expression vector pGEX-4T-2 (manufactured and sold by Pharmacia Fine Chemicals AB, Sweden) which can be used for producing a fused protein containing glutathione S transferase, to thereby obtain expression plasmid vectors which can be used for producing polypeptides comprising amino acid sequences of SEQ ID NOs. 1, 2 and 3, respectively. Each of the thus obtained expression plasmid vectors respectively containing the sequences of SEQ ID NOs. 6, 7 and 8 is individually introduced to *E. Coli* strain DH5α, and the resultant cells are cultured on a selection medium containing ampicillin, to thereby select transformant cell strains having the above-mentioned expression plasmid vectors, respectively.

EXAMPLE 11
[Production of the tyrosine kinase peptide of the present invention]

First, a polyclonal antibody to be used for confirmation of the production of the tyrosine kinase peptide of the present invention is produced as follows. A peptide is synthesized, which has a structure such that cysteine is bonded to the N-terminus of a peptide comprised of the 488th to 507th amino acids of the amino acid sequence of SEQ ID NO. 5 (which 488–507 amino acid sequence of SEQ ID NO. 5 corresponds to the C-terminal portion of the amino acid sequence deduced from the nucleotide sequence of the tyrosine kinase gene of the present invention). Specifically, a peptide, having the amino acid sequence: Cys Pro Ala Ser Val Ser Gly Gln Asp Ala Asp Gly Ser Thr Ser Pro Arg Ser Gln Glu Pro, is synthesized by means of a peptide synthesizer. The obtained peptide is coupled with KLH (Keyhole Limpet Hemocyanin) through a thiol group, thereby obtaining a KLH-coupled peptide. The KLH-coupled peptide is employed as an immunogen. Specifically, the KLH-coupled peptide is mixed with Freund's adjuvant, and a rabbit is immunized with the resultant mixture. From the immunized rabbit, antiserum is obtained.

Each of the transformant cell strains obtained in Example 10 which can respectively produce polypeptides having the amino acid sequences of SEQ ID NOs. 4 and 5 is individually solubilized with RIPA buffer [containing 0.1% SDS, 1% Triton X-100, 0.1% sodium deoxycholate, 20 mM Tris-HCl (PH 7.4), 1 mM PMSF, and 0.2 U/ml aprotinin], and the protein content of the cell is quantitatively determined. Then, the cell-derived protein is subjected to a thermal denaturation with SDS and then to an SDS-polyacrylamide gel electrophoresis (SDS-PAGE). After completion of the electrophoresis, the protein is blotted against a PVDF filter (manufactured and sold by Bio-Rad laboratories, USA), and the resultant protein-blotted filter is reacted with each of the above-mentioned antiserum and serum obtained from the rabbit prior to the immunization, individually, and then reacted with a peroxidase-labeled mouse monoclonal antibody against rabbit antibody. Subsequently, the protein blotted on the filter, which protein has been reacted with the peroxidase-labeled monoclonal antibody, is allowed to emit fluorescence by means of ECL Western Blot Detection System (manufactured and sold by Amersham International, U.K.) and the fluorescence was recorded on a photosensitive film, thereby detecting the protein. By comparing the results obtained with respect to the antiserum with the results obtained with respect to the prior-to-immunization serum, it is confirmed that the tyrosine kinase polypeptide of the present invention, having a molecular weight of about 55 kilodalton, has been produced.

The cell strains obtained in Example 10 which can respectively produce polypeptides having amino acid sequences of SEQ ID NOs. 1, 2 and 3 are individually inoculated in a liquid medium for E. Coli, which contains ampicillin, and incubated overnight. Subsequently, the incubated cells are diluted 10-fold with the same liquid medium and further incubated for 2 hours, and IPTG is added thereto so that the final concentration of IPTG becomes 1 mM, followed by incubation for 5 hours, thereby inducing production of protein. Subsequently, the cells are collected by centrifugation, and suspended in PBS containing 1% Triton X-100. The suspended cells are disrupted by means of an ultrasonic cell disrupting apparatus (manufactured and sold by Taitec Corporation, Japan) while cooling with ice, and the disrupted cells are subjected to centrifugation, thereby obtaining a supernatant. The supernatant is subjected to SDS-PAGE in the same manner as mentioned above, thereby obtaining a protein. The obtained protein is blotted on a PVDF filter and reacted with an anti-GST goat antibody (manufactured and sold by Pharmacia Fine Chemicals AB, Sweden) and further reacted with a peroxidase-labeled rabbit antibody against goat antibody, and the detection of the protein is conducted in the same manner as mentioned above by using ECL Western Blot Detection System. As a result, it is confirmed that the cell strains have respectively produced a peptide having a molecular weight of about 33 kilodalton and having an amino acid sequence of SEQ ID NO. 1, a peptide having a molecular weight of about 35 kilodalton and having an amino acid sequence of SEQ ID NO. 2, and a peptide having a molecular weight of about 63 kilodalton and having an amino acid sequence of SEQ ID NO. 3. Next, these three types of GST-fused tyrosine kinase peptides are separated and purified from the disrupted cells by using a glutathione Sepharose column (manufactured and sold by Pharmacia Fine Chemicals AB, Sweden) in accordance with the manual accompanying the column. The thus obtained purified peptides are subjected to SDS-PAGE and Coomassie staining, to thereby confirm the respective molecular weights of these peptides determined by the above western blotting.

EXAMPLE 12

[Confirmation of the enzyme activity of the tyrosine kinase of the present invention]

Each of the transformant cell strains obtained in Example 10 which can respectively produce polypeptides having the amino acid sequences of SEQ ID NOs. 4 and 5 is individually placed in a 1.5 ml-volume Eppendorf tube, and RIPA buffer is added to the cells to thereby solubilize the cells. Protein G Sepharose gel (manufactured and sold by Pharmacia Fine Chemicals AB, Sweden) is added to the solubilized cells, and the resultant mixture is gently stirred at 4° C. overnight to thereby effect a reaction. Subsequently, the resultant reaction mixture is subjected to centrifugation, thereby precipitating protein G Sepharose gel and substances which have reacted nonspecifically to the protein G, followed by removal thereof. Thus, a disrupted cell suspension containing the tyrosine kinase polypeptide of the present invention is obtained. The anti-tyrosine kinase polyclonal antibody obtained in Example 11 is added to the disrupted cell suspension, and a reaction is conducted at 4° C. for 1 hour. Subsequently, protein G Sepharose gel is added thereto and gently stirred at 4° C. for 1 hour to thereby effect a reaction. Then, a centrifugation is conducted to thereby cause the protein G Sepharose gel which has adsorbed the tyrosine kinase of the present invention to be separated as a precipitated fraction. The separated fraction is washed with the above-mentioned RIPA buffer, and then subjected to centrifugation in the same manner as described above. This operation is conducted three times. Thus, the tyrosine kinase polypeptide of the present invention which has been adsorbed on protein G Sepharose gel is obtained.

With respect to each of the above-obtained tyrosine kinase polypeptide adsorbed on the gel and the polypeptide obtained in Example 11 comprising the amino acid sequence of SEQ ID NO. 3, the enzyme activity of tyrosine kinase is evaluated using a tyrosine kinase assay kit which is of a non-radioreactive type (manufactured and sold by Boehringer-Mannheim GmbH, Germany). The assay is conducted in accordance with the manual accompanying the kit. As a result, it is confirmed that both of the polypeptides have enzyme activity of tyrosine kinase.

EXAMPLE 13

[Screening of chemical substances by utilizing the tyrosine kinase of the present invention]

Using the tyrosine kinase polypeptide of the present invention which has been purified by the method described in Example 12 and the tyrosine kinase polypeptide of the present invention which has been purified by the method described in Example 11, a substance having the capability to inhibit the tyrosine kinase activity of the tyrosine kinase of the present invention is searched with respect to supernatants of cultures of various Actinomycete cell lines, utilizing the above-mentioned capability as a criterion for detection, and the detected substance is isolated and purified from the culture supernatant, and identified.

Specifically, about 1,000 cell lines of Actinomycetes are individually cultured to obtain culture supernatants. The supernatants are individually subjected to filtration to obtain filtrates, and an equivolume of butyl acetate is added to each supernatant to thereby effect extraction. The extracted 1,000 types of substances are individually dried in vacuo to obtain the substances in a powdery form.

Substances which inhibit tyrosine kinase activity are screened from the above-obtained powdery substances by an assay method in which the tyrosine kinase assay kit described in Example 12 and either of the polypeptides respectively having the sequences of SEQ ID NOs. 4 and 5 are used to find out substances which lower the absorbance measured with respect to the tyrosine kinase polypeptide of the present invention. More illustratively, the obtained 1,000 different powdery substances are tested with respect to the capability to lower the absorbance 30% or more, based on the absorbance as measured with respect to the tyrosine kinase polypeptide without adding the powdery substance. As a result, about 50 different powdery substances are found to have the capability.

Of those substances, one powdery substance is selected, and aliquots of the selected powdery substance are dissolved in chloroform, methanol and distilled water, respectively. The resultant solutions are individually subjected to filtration, and the resultant filtrates are individually dried in vacuo to thereby obtain powdery materials. Each of the obtained powdery materials is assayed in the same manner as mentioned above and, as a result, it is confirmed that the powdery material derived from the methanol-solubles has an inhibitory activity for the tyrosine kinase of the present invention. The methanol-solubles are fractionated in a reverse phase column by high-speed liquid chromatography. A peak of each of the these fractions is collected using a fraction collector. Each of the collected fractions is further assayed in the same manner as mentioned above and, as a result, it is found that one of the fractions has an inhibitory activity for the tyrosine kinase of the present invention. The fraction is dried in vacuo to thereby obtain a powder, and the powder is analyzed by mass spectography, NMR and IR. As a result, it is found that the molecular formula of the substance of the above fraction is $C_9H_9NO_3$. When a data base of chemical substances is searched to identify the substance, based on the chemical shifts obtained by NMR and the spectra obtained by IR, it is found that the substance is identical to erbstatin (see Umezawa et al., J. Antibiot. 39: 170, 1986). Erbstatin is known as a specific inhibitor for a tyrosine kinase. These results show that the method of screening chemical substances using the tyrosine kinase of the present invention is effective for detecting useful chemical substances having the capability to inhibit or activate tyrosine kinase activity.

INDUSTRIAL APPLICABILITY

The tyrosine kinase of the present invention can be advantageously used for screening chemical substances having the capability to inhibit or activate the tyrosine kinase activity of at least the tyrosine kinase of the present invention. Further, the tyrosine kinase of the present invention and the gene coding therefor can be advantageously used for estimating or controlling the differentiation of blood cells. The gene coding for the tyrosine kinase of the present invention can be utilized for evaluation of various pharmaceuticals and for culturing blood stem cells without causing differentiation thereof. Further, it is expected that the gene coding for the tyrosine kinase of the present invention can be utilized for development of a carcinostatic agent and for gene therapy.

I claim:

1. An isolated polypeptide having tyrosine kinase activity, comprising an amino acid sequence selected from the group consisting of SEQ ID NOs. 1, 2, 3, 4 and 5.

2. An isolated deoxyribonucleic acid coding for a polypeptide having tyrosine kinase activity, said polypeptide comprising an amino acid sequence selected from the group consisting of SEQ ID NOs. 1, 2, 3, 4 and 5.

3. A replicable recombinant DNA molecule comprising a replicable expression vector and, operably inserted in said vector, a deoxyribonucleic acid coding for a polypeptide having tyrosine kinase activity, said polypeptide comprising an amino acid sequence selected from the group consisting of SEQ ID NOs. 1, 2, 3, 4 and 5.

4. A microorganism or animal cell transformed with a replicable recombinant DNA molecule comprising a replicable expression vector and, operably inserted in said vector, a deoxyribonucleic acid coding for a polypeptide having tyrosine kinase activity, said polypeptide comprising an amino acid sequence selected from the group consisting of SEQ ID NOs. 1, 2, 3, 4 and 5.

5. A method of screening for chemical substances having the capability to inhibit or activate tyrosine kinase activity, which comprises:

contacting a sample material with a polypeptide comprising an amino acid sequence selected from the group consisting of SEQ ID NOs. 1, 2, 3, 4 and 5 to detect a chemical substance having the capability to inhibit or activate the tyrosine kinase activity of at least said polypeptide, wherein said capability of said chemical substance is utilized as a criterion for the detection; and isolating said detected chemical substance from the sample material.

* * * * *